(12) United States Patent
Kulkarni

(10) Patent No.: US 9,702,807 B2
(45) Date of Patent: Jul. 11, 2017

(54) MEASUREMENT OF SERUM LIPOPROTEINS

(71) Applicant: ATHEROTECH, INC., Birmingham, AL (US)

(72) Inventor: Krishnaji R Kulkarni, Vestavia, AL (US)

(73) Assignee: Ningbo Alabama, LLC, Birmingham, AL (US)

(*) Notice: Subject to any disclaimer, the term of this patent is extended or adjusted under 35 U.S.C. 154(b) by 27 days.

(21) Appl. No.: 14/408,527

(22) PCT Filed: Jun. 17, 2013

(86) PCT No.: PCT/US2013/046170
§ 371 (c)(1),
(2) Date: Dec. 16, 2014

(87) PCT Pub. No.: WO2013/188879
PCT Pub. Date: Dec. 19, 2013

(65) Prior Publication Data
US 2015/0146205 A1 May 28, 2015

Related U.S. Application Data

(63) Continuation-in-part of application No. 13/842,577, filed on Mar. 15, 2013, now Pat. No. 9,239,280.
(Continued)

(51) Int. Cl.
*G01N 15/14* (2006.01)
*G01N 15/06* (2006.01)
(Continued)

(52) U.S. Cl.
CPC ......... *G01N 15/1434* (2013.01); *G01N 15/06* (2013.01); *G01N 33/491* (2013.01);
(Continued)

(58) Field of Classification Search
CPC .. G01N 15/1434; G01N 33/92; G01N 33/491; G01N 15/06; G01N 2015/1486; G01N 33/492
(Continued)

(56) References Cited

U.S. PATENT DOCUMENTS

| 4,987,085 A | 1/1991 | Allen |
| 5,187,068 A * | 2/1993 | Luca ................. G01N 33/6878 |
| | | 435/11 |

(Continued)

FOREIGN PATENT DOCUMENTS

| JP | 2002-243745 | 8/2002 |
| JP | 2002243745 A | 8/2002 |

(Continued)

OTHER PUBLICATIONS

Kulkarni, et al. "Quantification of cholesterol in all lipoprotein classes by VAP-II method" 1994; Journal of Lipid Research, vol. 35, pp. 159-168.
(Continued)

*Primary Examiner* — Sang Nguyen
(74) *Attorney, Agent, or Firm* — Thomas G. Peterson; Bradley Arant Boult Cummings LLP

(57) ABSTRACT

Although a more accurate estimate of a person's risk of cardiovascular disease can be made on the basis of the number of lipoprotein particles per unit volume in the person's blood, current methods all rely on measuring the mass of lipoprotein cholesterol per unit volume. It has been discovered that a rapid and accurate lipoprotein particle count can be obtained by photometry. A method and apparatus are provided for measuring the number of lipoprotein particles in a sample using photometry.

15 Claims, 32 Drawing Sheets

Related U.S. Application Data

(60) Provisional application No. 61/815,503, filed on Apr. 24, 2013, provisional application No. 61/660,710, filed on Jun. 16, 2012.

(51) Int. Cl.
 *G01N 33/49* (2006.01)
 *G01N 33/92* (2006.01)

(52) U.S. Cl.
 CPC ........... *G01N 33/92* (2013.01); *G01N 33/492* (2013.01); *G01N 2015/1486* (2013.01)

(58) Field of Classification Search
 USPC ................ 356/335–343, 36–41, 317–318
 See application file for complete search history.

(56) References Cited

U.S. PATENT DOCUMENTS

| | | | |
|---|---|---|---|
| 5,411,053 A | 5/1995 | Markham | |
| 5,460,974 A | 10/1995 | Kozak et al. | |
| 5,589,080 A | 12/1996 | Cho | |
| 5,633,168 A | 5/1997 | Glasscock | |
| 5,766,552 A | 6/1998 | Doshi | |
| 5,872,622 A | 2/1999 | Schildmeyer et al. | |
| 5,895,869 A | 4/1999 | Von Behrens | |
| 5,928,484 A | 7/1999 | Bellon et al. | |
| 6,212,916 B1 | 4/2001 | Carr | |
| 6,737,275 B2 | 5/2004 | Purdie et al. | |
| 7,521,248 B2 | 4/2009 | Kulkarni | |
| 7,700,360 B2 | 4/2010 | Everhart et al. | |
| 7,856,323 B2 | 12/2010 | Troup | |
| 2003/0136680 A1 | 7/2003 | Benner et al. | |
| 2003/0235918 A1* | 12/2003 | Shewmake | C25B 1/285 436/13 |
| 2004/0203070 A1 | 10/2004 | Sovolainen et al. | |
| 2005/0233439 A1 | 10/2005 | Everhart et al. | |
| 2007/0044789 A1 | 3/2007 | Greico | |
| 2007/0062583 A1 | 3/2007 | Cox | |
| 2008/0038762 A1 | 2/2008 | Troup | |
| 2008/0121025 A1 | 5/2008 | Okazaki | |
| 2010/0267631 A1 | 10/2010 | Dasseux et al. | |
| 2012/0052594 A1* | 3/2012 | Guadagno | G01N 33/92 436/501 |
| 2012/0122959 A1* | 5/2012 | Stoffel | C12N 15/113 514/44 A |
| 2012/0244555 A1* | 9/2012 | Blyth | G01N 33/92 435/7.9 |
| 2012/0315706 A1 | 12/2012 | Caulfield et al. | |

FOREIGN PATENT DOCUMENTS

| | | |
|---|---|---|
| JP | 3819895 | 9/2006 |
| JP | 2010-048703 | 3/2010 |

OTHER PUBLICATIONS

Chang, Bong Ho "International Search Report and Written Opinion—International application No. PCT/US2013/04170" Korean Intellectual Property Office; Sep. 13, 2013; pp. 1-13.

\* cited by examiner

MEASUREMENT OF SERUM LIPOPROTEINS

CROSS-REFERENCE TO RELATED APPLICATIONS

This application is a national stage under 35 U.S.C. 371 of International Application PCT/US2013/046170, filed on Jun. 17, 2013 (currently pending). International Application no. PCT/US2013/046170 cites the priority of U.S. provisional patent application no. 61/815,503, filed Apr. 24, 2013. International Application PCT/US2013/046170 is a continuation in part of U.S. patent application Ser. No. 13/842,577, filed Mar. 15, 2013 (currently pending). U.S. patent application Ser. no. 13/842,577 cites the priority of U.S. provisional patent application No. 61/660,710 filed Jun. 16, 2012.

BACKGROUND

The measurement of blood lipoproteins is critical in predicting an individual's risk of many chronic diseases, particularly cardiovascular disease such as coronary heart disease (CHD). CHD continues to be the leading cause of death in the United States despite phenomenal advances made in its diagnosis, treatment, and prevention in the last 3 decades. As per the recently released Heart and Stroke Statistics (2012 Update by the American Heart Association; Circulation 2012; 125:e2-e220), CHD accounts for 1 in 6 deaths in the US. In 2008 as many as 405,309 people died of CHD and 785,000 were expected to have a new heart attack and another 470,000 people with recurrent attacks. These astounding statistics clearly tell us that prevention of heart disease still remains a formidable task.

Heart disease is a multi-factorial disease and several risk factors such as high blood pressure, smoking, elevated serum low density lipoprotein (LDL) cholesterol, and diabetes are attributed to an increased risk. Among these risk factors, LDL is known to be directly responsible for the build-up of the plaque within the arterial wall which results in subsequent coronary events. This is further supported by the fact that lowering LDL cholesterol by pharmacological means or lifestyle changes significantly reduces coronary events. However, only 50% of coronary events can be accounted by elevated LDL cholesterol and many studies suggest that coronary events can also occur even in people with normal LDL cholesterol. Therefore, in recent years there has been a surge in research in identifying new risk factors and biomarkers that may explain the CHD risk that cannot not be accounted by traditional risk factors. Some examples of emerging risk factors are high sensitivity C-Reactive Protein (hs-CRP), homocysteine, lipoproteins other than LDL cholesterol, such as low levels of high density lipoproteins (HDL) and its subclasses HDL2 and HDL3, and non-HDL cholesterol which includes intermediate density lipoproteins (IDL), very low density lipoproteins (VLDL), and lipoprotein(a) [Lp(a)] in addition to LDL cholesterol. Several other studies also support measurement of apolipoproteins, the proteins on the surface of lipoprotein particles. In particular, evidence to measure serum apolipoprotein B (apo B) is compelling since all atherogenic lipoproteins (Lp(a), LDL, IDL and VLDL) contain apo B and thus truly reflects the comprehensive risk associated with all atherogenic lipoproteins. In addition, serum apolipoprotein concentration also reflects the total number of atherogenic particles, which are responsible for the plaque build-up, because each of these contain one and only one molecule of apo B.

More recent studies also suggest that LDL particle (LDLp) concentration (or number) is also an independent risk marker and is superior to the risk predicted by routinely measured LDL cholesterol (more often calculated using Friedewald equation in most labs). A recent study suggests that LDL particles, not the amount of cholesterol carried by them, play a pivotal role in the development of atherosclerosis. It appears that endothelial retention of intact apo B containing particles is essential for initiation of atherosclerotic process. Thus, cholesterol in LDL molecules merely acts as 'passenger' while particles act as the 'driver'. A number of published outcome studies, which used LDL particle number measurement by nuclear magnetic resonance (NMR), suggest LDL particle number is a significant and independent predictor of cardiovascular endpoints, including CHD death and myocardial infarction. Most of these studies also have demonstrated that the risk associated with elevated LDL particle number is much higher than that associated with LDL cholesterol.

As mentioned above there is sufficient evidence that increased numbers of lipoproteins other than LDL, such as elevated levels of atherogenic Lp(a), IDL, and VLDL, and low levels of anti-atherogenic HDL, are also strongly and independently associated with CHD. Thus, based on the observed clinical benefits of LDL particle concentration measurement over LDL cholesterol the measurement of particle concentration (or number) of other lipoproteins such as Lp(a), IDL, VLDL, and HDL would also result in clinical benefit and thus diagnosis and management of heart disease.

Even though an independent association of LDL particle number (LDLp) is known, LDLp number (as well as the particle number of other lipoproteins) is not commonly measured because of the following reasons. First, measurement of cholesterol is relatively easy since several simple enzymatic methods are available. Second, LDL cholesterol can be conveniently calculated using Friedewald equation [LDL-C=Total Cholesterol-(HDL cholesterol+0.2*triglycerides)]. Third, methods to measure lipoprotein particle number, including LDLp, are very few, not widely available and are complicated and expensive. The three currently available commercial assays for LDLp are based upon 1) NMR (LipoScience, NC); 2) ion mobility (Quest Diagnostics, CA); and 3) ultracentrifugation with fluorescence detection (Spectracell, TX). Furthermore, the above measurement methods do not measure the particle number of all lipoprotein classes. As a result, the particle number measurement methods cannot meet the demand for this widely required test.

Consequently, there is a long-felt but unmet need in the art to develop newer, simpler, and more accurate methods for the measurement of lipoprotein particle number, including, but not limited to, HDL, Lp(a), LDL, IDL and VLDL particle number. Particularly, there is a need to develop newer, simpler, and more accurate methods the measurement of lipoprotein particle number, including, but not limited to, HDL, Lp(a), LDL, IDL and VLDL particle number, which can be performed inexpensively in the clinical context, and which has the ability to enumerate particles of all significant types of lipoprotein. The present disclosure addresses such needs.

SUMMARY

The following presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The disclosure provides methods and apparatuses for determining (i.e. counting) lipoprotein particle numbers in a sample. In one aspect, the sample is a blood sample. In another aspect the sample is a blood serum sample. In one aspect, the lipoprotein particle number is determined photometrically. It has been unexpectedly discovered that photometric measurements of lipoproteins in a sample provide a rapid, inexpensive, and accurate determination (count) of lipoprotein particle number. It has also been unexpectedly discovered that photometric measurement can be used effectively to determine (count) lipoprotein particle numbers in sample that has been fractionated to provide for separation of the various classes of lipoprotein particles. The fractionation may be a complete or partial fractionation. In one aspect, density-gradient ultracentrifugation is used as the fractionation technique. In one aspect, light scattering measurements are employed as the photometric measurement. The methods disclosed have been found to provide accurate determination (count) of lipoprotein particle number and to be robust in the presence of blood and serum components.

A general embodiment of the method comprises obtaining a photometric measurement of a serum lipid fraction from a subject and calculating a particle count for at least one serum lipid in the serum lipid fraction, where the particle count is a function of the photometric measurement. In one aspect, the photometric measurement is a measurement of light scattering caused by the serum lipid. The serum lipid fraction may be fractioned, either completely or partially, prior to the photometric measurement being obtained.

Another general embodiment of the method comprises obtaining a photometric measurement of a lipoprotein particle in a serum lipid fraction from a subject and calculating a particle count for at least one lipoprotein particle in the lipid fraction, where the particle count is a function of the photometric measurement. In one aspect, the photometric measurement is a measurement of light scattering caused by the lipoprotein particle. The serum lipid fraction may be fractioned, either completely or partially, prior to the photometric measurement being obtained.

A more particular embodiment of the method comprises separating at least an LDL fraction in a sample, obtaining a measurement of the light scattering from the LDL fraction and calculating a particle count for the LDL fraction, wherein the particle count is a function of the measurement of light scattering. The method may further comprise separating additional fractions in the sample in addition to the LDL fraction, such as a an HDL fraction, a Lp(a) fraction, an IDL fraction and a VLDL fraction, obtaining a measurement of the light scattering from at least one of the additional fractions and calculating a particle count for each of the additional fractions from which a light scattering measurement was obtained, wherein the particle count is a function of the measurement of light scattering.

A more particular embodiment of the method comprises separating at least an LDL fraction and an IDL fraction in a sample, obtaining a measurement of the light scattering from at least one of the LDL and IDL fractions and calculating a particle count for each of the fractions from which a light scattering measurement was obtained, wherein the particle count is a function of the measurement of light scattering. The method may further comprise separating additional fractions in the sample in addition to the foregoing, such as a an HDL fraction, a Lp(a) fraction and a VLDL fraction, obtaining a measurement of the light scattering from at least one of the additional fractions and calculating a particle count for each of the additional fractions from which a light scattering measurement was obtained, wherein the particle count is a function of the measurement of light scattering.

A more particular embodiment of the method comprises separating at least an LDL fraction, an IDL fraction and a VLDL fraction in a sample, obtaining a measurement of the light scattering from at least one of the fractions and calculating a particle count for each of the fractions from which a light scattering measurement was obtained, wherein the particle count is a function of the measurement of light scattering. The method may further comprise separating additional fractions in the sample in addition to the foregoing, such as a Lp(a) fraction and a HDL fraction in a sample, obtaining a measurement of the light scattering from at least one of the additional fractions and calculating a particle count for each of the additional fractions from which a light scattering measurement was obtained, wherein the particle count is a function of the measurement of light scattering.

In one embodiment, the method comprises separating at least an HDL fraction, an LDL fraction, an IDL fraction and a VLDL fraction in a sample, obtaining a measurement of the light scattering from at least one of the fractions and calculating a particle count for each of the fractions from which a light scattering measurement was obtained, wherein the particle count is a function of the measurement of light scattering. The method may further comprise separating an Lp(a) fraction, obtaining a measurement of the light scattering from the Lp(a) fraction and calculating a particle count for the Lp(a) fraction, wherein the particle count is a function of the measurement of light scattering.

In one embodiment, the method comprises separating at least an HDL fraction, an Lp(a) fraction, an LDL fraction, an IDL fraction and a VLDL fraction in a sample, obtaining a measurement of the light scattering from at least one of the fractions and calculating a particle count for each of the fractions from which a light scattering measurement was obtained, wherein the particle count is a function of the measurement of light scattering.

In one embodiment, the method comprises separating at least an HDL fraction in a sample, obtaining a measurement of the light scattering from the HDL fraction and calculating a particle count from the HDL fraction, wherein the particle count is a function of the measurement of light scattering.

In one embodiment, the method comprises separating at least an Lp(a) fraction in a sample, obtaining a measurement of the light scattering from the Lp(a) fraction and calculating a particle count from the Lp(a) fraction, wherein the particle count is a function of the measurement of light scattering.

In one aspect of the foregoing methods, a particle count is obtained for a fraction other than the LDL fraction, such as a HDL fraction, an Lp(a) fraction, an IDL fraction and a VLDL fraction.

An apparatus for determining a lipoprotein particle count from a sample is provided. A general embodiment of the apparatus comprises a containing means for containing a liquid sample having stratified lipid/lipoprotein fractions, a conveying means for conveying the sample from the containing means to a means for counting particles and means for counting particles configured to receive the sample from the containing means by way of the conveying means.

Another general embodiment of the apparatus comprises a sample vessel containing the sample having stratified lipid/lipoprotein fractions; a liquid conduit positioned to collect the sample from the bottom of the sample vessel; and a light scattering counter positioned to receive the sample from the conduit.

Also provided is a method of calibrating the measurement of particle count of an atherogenic lipoprotein comprising obtaining a photometric measurement of an atherogenic lipoprotein from a calibration sample, measuring the molar concentration of apolipoprotein B (apoB) in the calibration sample, and calculating a regression between the photometric measurement and the molar concentration of apoB.

DETAILED DESCRIPTION

A. Definitions

Figure 1A:
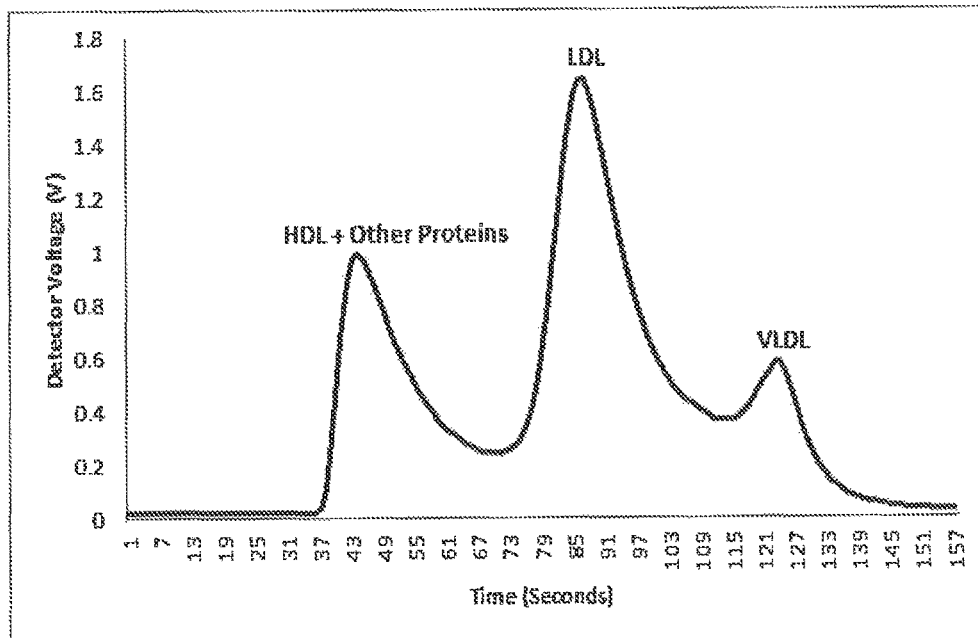
FIG. 1A is an exemplary particle concentration profile collected with a light scattering detector showing a profile with low amounts of Lp(a) and IDL showing a distinct peak corresponding to HDL, LDL and VLDL.

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "about" as used herein refers to a value that is within a range around a central value, the range being a margin of error that would be expected by one of ordinary skill in the art based on accepted methods of measurement of the particular central value.

The terms "approximate" and "approximately" as used herein refer to a difference between an actual relationship between two variables and a calculated regression between the two variables that is relatively minor. For example, such a relationship with a variance above 0.5 or below −0.5 could be said to approximate the calculated regression.

B. Lipoproteins

Prior to describing the methods and apparatus disclosed herein, the nature and functions of lipoprotein particles are discussed. Lipoproteins are spherical particles circulating in the blood whose primary function is to provide fuel in the form of fat and cholesterol. Cholesterol is an essential structural component of cell wall and a precursor to many hormones. Thus all lipoprotein particles consist of a dense hydrophobic core tightly packed with triglycerides (the main source of energy) and cholesterol ester surrounded by a thin hydrophilic layer consisting of phospholipids, free cholesterol, and unique proteins called apolipoproteins. This structural arrangement allows the easy transport of these particles in the hydrophilic medium of blood from their origin in the gut and liver to the peripheral cells. The chemical composition of lipoproteins varies depending upon their function, origin, and metabolic state, and results in different densities and sizes of lipoproteins. Thus, lipoproteins are primarily classified based on their density into the following classes: HDL, Lp(a), LDL, IDL and VLDL. HDL is a lipoprotein rich in proteins. LDL is a lipoprotein rich in cholesterol and containing decreased amounts of triglyceride (TG). VLDL lipoproteins are rich in TG. Lp(a), which is an LDL particle with a unique protein called apolipoprotein(a) attached to the apoB molecule of the LDL particle through a disulfide bond; Lp(a) particle share many of the characteristics of LDL particles. IDL lipoproteins have a density between LDL and VLDL and are rich in TG but low in cholesterol.

Since all lipoproteins have similar structural components (i.e., all contain cholesterol, triglycerides, and phospholipids) with unique apolipoproteins their separation for the purpose of quantitation based on chemical composition is difficult. As a result, the different physical parameters of lipoproteins, such as, but not limited to, density and size, are most commonly utilized for separation purposes. Ultracentrifugation and electrophoresis are the most common and accepted separation methods, although methods based on chemical composition have recently emerged.

C. General Overview of Method

The measurement of lipoprotein particle concentration (number) is based on the direct relationship between the number of lipoprotein particles present in a given volume of sample and the area under the lipoprotein peak as determined by the detector. As discussed herein, during the separation step, (such as, but not limited to, ultracentrifugation) lipoproteins are separated based upon their respective densities. When ultracentrifugation is used in the separation step, the HDL migrates to the bottom of the centrifuge tube, LDL migrates to the middle of the tube, and VLDL migrates to the top of tube. Lp(a) migrates between HDL and LDL, and IDL migrates between LDL and VLDL. Thus, as lipoproteins elute sequentially from the bottom of the centrifuge tube and pass through the detector (such as photometric detector or a light scattering detector as discussed in more detail herein), a signal is generated by the detector. The signal from the detector is output as a continuous curve corresponding to particle concentration profile, with peaks corresponding to the various lipoproteins (including HDL and other proteins, Lp(a), LDL, IDL, and VLDL) that are present in the sample.

Figure 1B:
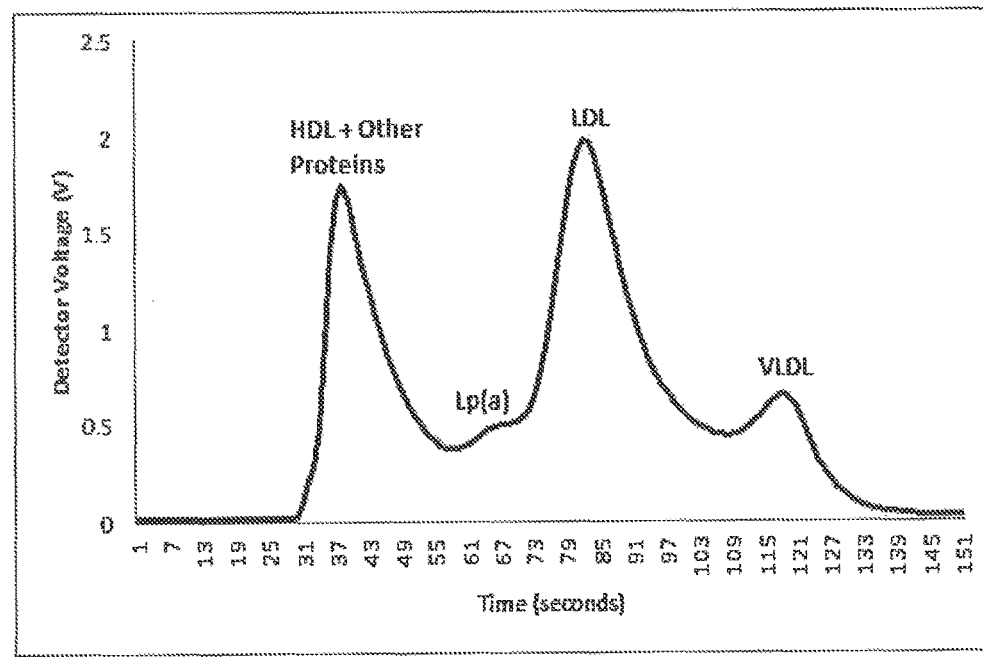
FIG. 1B is an exemplary particle concentration profile collected with a light scattering detector showing a profile with a distinct Lp(a) peak and also showing distinct HDL, LDL and VLDL peaks.
Figure 1C:
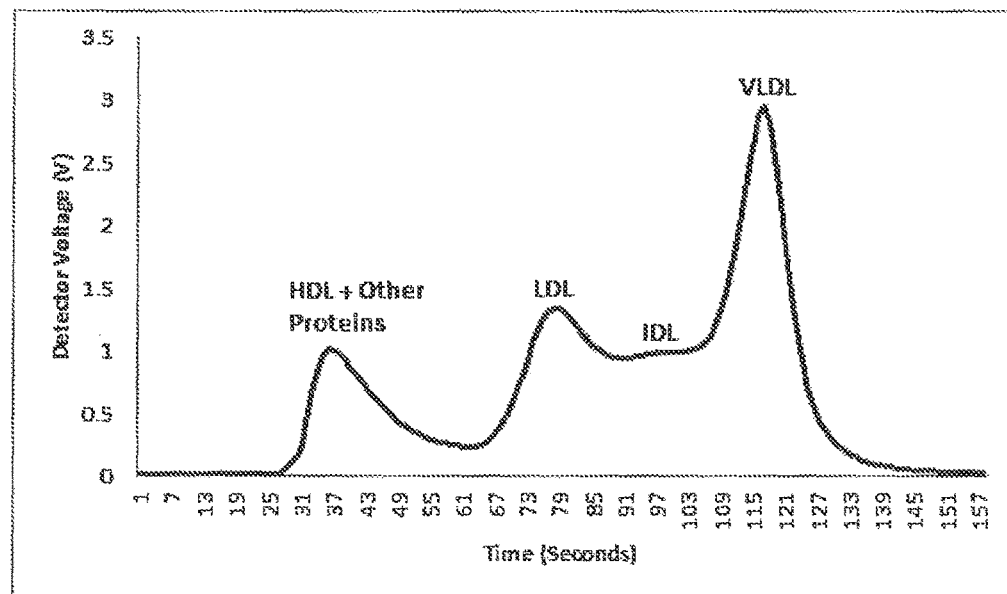
FIG. 1C is an exemplary particle concentration profile collected with a light scattering detector showing a distinct IDL peak and also showing distinct HDL, LDL and VLDL peaks.

When a light scattering detector is used, the detector output is a continuous curve corresponding to the scattered light intensity (in volt-minutes) (described in more detail herein). Three examples of particle concentration profiles collected with a light scattering detector are shown in FIG. 1A-C. The profiles shown in FIG. 1A-C were obtained using the centrifugation conditions described as Condition 1 herein and using the apparatus and methods disclosed in more detail herein. FIG. 1A is a profile with low amounts of Lp(a) and IDL showing a distinct peak corresponding to HDL, LDL and VLDL; FIG. 1B is a profile showing a distinct Lp(a) peak and also showing distinct HDL, LDL and VLDL peaks; and FIG. 1C is a profile showing a distinct IDL peak and also showing distinct HDL, LDL and VLDL peaks.

As can be seen from the profiles in FIGS. 1A-C, the separation of lipoprotein peaks from each other does not reach baseline separation since the separation procedure used, in this case ultracentrifugation, is a rapid non-equilibrium density gradient ultracentrifugation suitable for higher throughput required by a clinical laboratory. Thus, quantitation of each lipoprotein requires a mathematical deconvolution process to calculate the corresponding areas under the respective lipoprotein peaks. The deconvolution process quantifies lipoprotein peaks in terms of their respective peak areas, which can be used to determine particle concentration as described herein.

The deconvolution process uses a general purpose computer to record the output from the detector. The deconvolution process is based upon the peak shapes (peak widths at half-height and exponential tails) and sizes (peak height) expected and observed from the isolated individual lipoprotein classes from preparative ultracentrifugation. Fitted subcurves are configured to align with the shapes (peak width and exponential tail) and size (peak height) of the peaks on the main continuous curve. Furthermore, subcurve peak positions and shapes and sizes are adjusted so as to minimize the difference between the total area under the main continuous response curve from the detector and sum of the areas under all subcurves. The software uses a least-square non-linear regression analysis to minimize the area between the main response curve from the detector and sum of the subcurves corresponding to individual lipoprotein peaks.

Figure 1D:
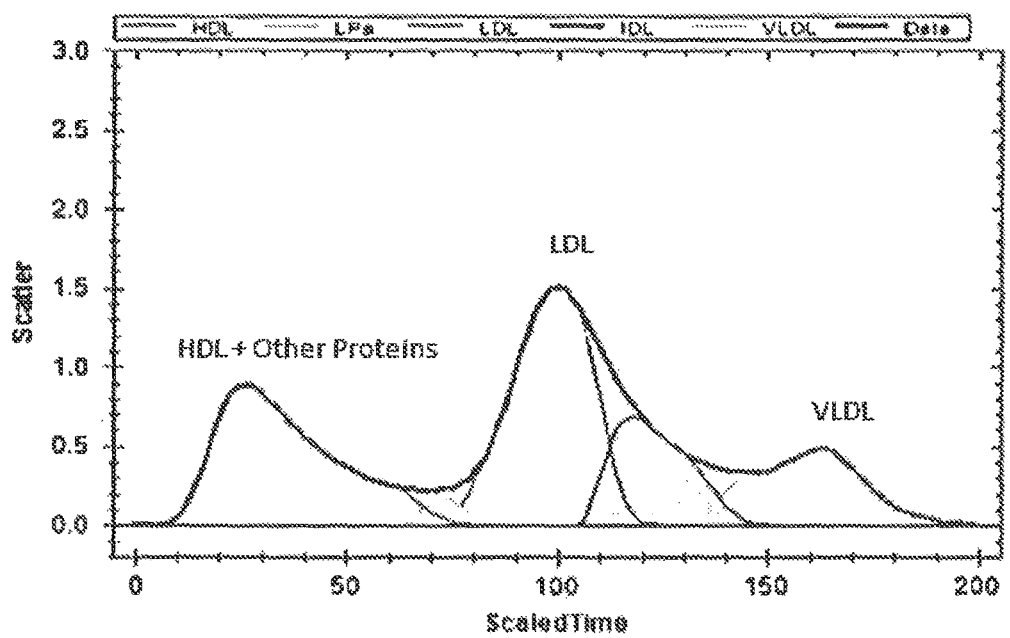
FIG. 1D is an exemplary deconvoluted profile corresponding to the particle concentration profile shown in FIG. 1A.
Figure 1E:
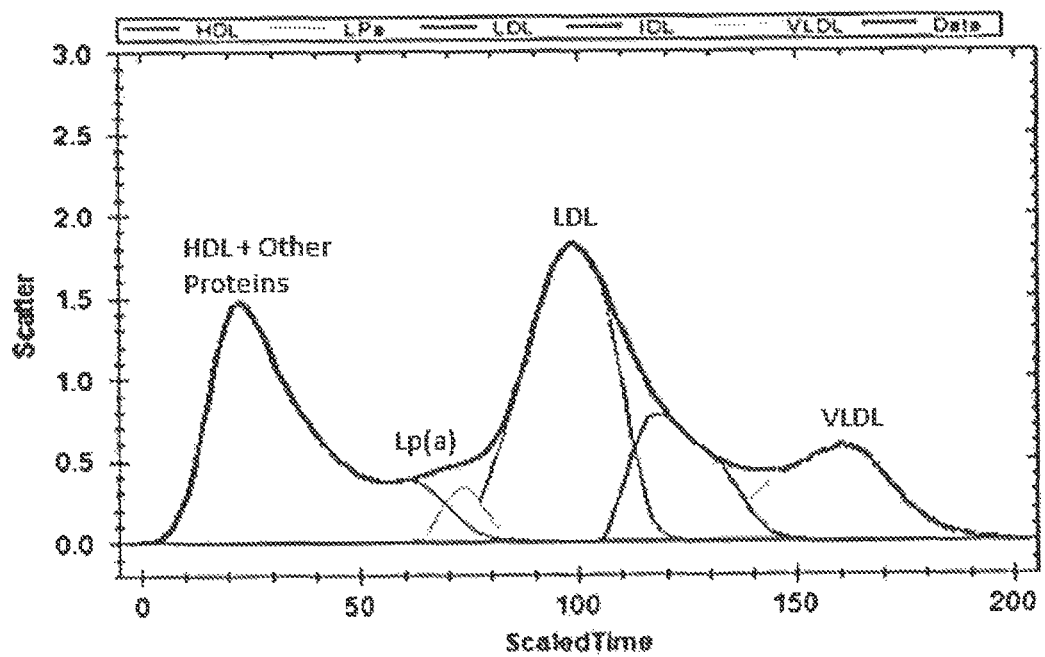
FIG. 1E is an exemplary deconvoluted profile corresponding to the particle concentration profile shown in FIG. 1B.
Figure 1F:
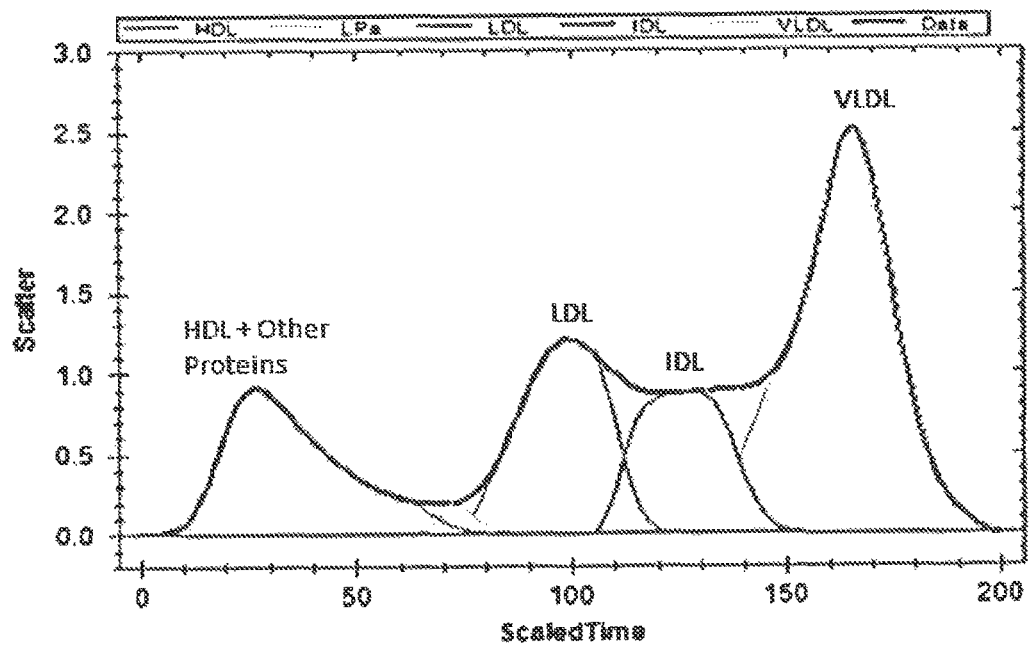
FIG. 1F is an exemplary deconvoluted profile corresponding to the particle concentration profile shown in FIG. 1C.

Exemplary deconvoluted profiles corresponding to raw profiles generated from the output of the detector as shown in FIGS. 1A-C are shown in FIGS. 1D-F. As can be seen, the deconvolution process generates subcurves for the lipoprotein classes discussed herein. From such subcurves, the area under each subcurve is calculated as is known in the art.

The area under each subcurve is then converted to a particle concentration (nmol/L) using a calibration procedure. Since all five lipoprotein classes have different sizes and varying composition, the amount of light scattered from each lipoprotein type of particle is different (for example, IDL is larger than LDL so an IDL particle scatters a greater amount of light than an LDL particle). Therefore, each lipoprotein class requires a separate calibration curve.

Since there are no materials available with known concentration of lipoprotein particles, a novel approach using a marker specific for a given lipoprotein particle was used. While a number of specific markers may exist and be used, in the present disclosure the specific marker for the atherogenic lipoproteins (Lp(a), LDL, IDL and VLDL) was apo B and the specific marker for HDL was apo A1. From the art, it is known that each atherogenic lipoprotein particle contains one and only one apo B molecule and that each particle of HDL contains from 2-5 particles of apo A1. Thus, the number of lipoprotein particles in a given fraction can be calculated if the marker concentration in that fraction is known.

Fractions are collected for analysis of the marker and the amount of marker in the sample is determined (such as through the use of an immunoassay) in mg/dL. Since the volume of the fraction is known, the concentration of marker in mg may be determined. The molar concentration of marker is then determined using the molecular weight of the marker. In addition, the area under a given lipoprotein curve is directly proportional to the number or concentration of lipoprotein particles. Thus, if the area under a lipoprotein curve is calibrated using materials with known amount of a specific marker, one can calculate the amount of the marker in a lipoprotein peak of unknown patient (in moles) using calibration curve method (as commonly used for many diagnostic tests) and thus the number of LDL or other lipoprotein particles (using Avogadro's concept).

A specific example of the calibration procedure is provided using LDL as an example. Calibration procedures for the remaining atherogenic lipoproteins will be carried out in the same manner. For calibration, fresh patients serum samples with a wide ranging apo B concentration (previously determined using immunoassay methods) were used as calibration materials. The calibration samples are subject to separation as described herein; in one embodiment, the separation and analysis procedure for the calibration samples is the same as the separation procedure used for determining lipoprotein particle concentration in an unknown sample (for example, Conditions 1 and/or 2 as described herein). Rather than analyzing the centrifugate using a photometric detector, the fractions are collected for measurement of the concentration of apo B, the specific marker. Any method of apo B measurement may be used. In one aspect, an immunoassay method, such as the Abbott/Architect C8000 system, is used to determine apo B amount in mg/dL. The concentration of apo B in absolute mg in each fraction can be calculated by knowing the volume of each fraction (which can be measured easily). On examining the profile curves generated, for example profile curves from the same sample, one can determine which of the examined fractions correspond to the LDL peak (or any desired lipoprotein peak). The fractions corresponding to LDL are summed to yield a final apo B amount. The apo B amount is used as Y axis and the LDL peak area as X-axis to plot the calibration curve. The process is repeated for each sample to generate a calibration curve.

In order to find apo B concentration in LDL of unknown sample, equation 1 is used $$Y = mx + c \qquad \text{Equation 1}$$

Y is the LDL apo B concentration which is to be determined;
m is the slope of calibration curve;
x is the LDL peak area in V·min; and
C is intercept of calibration curve.

Figure 2:
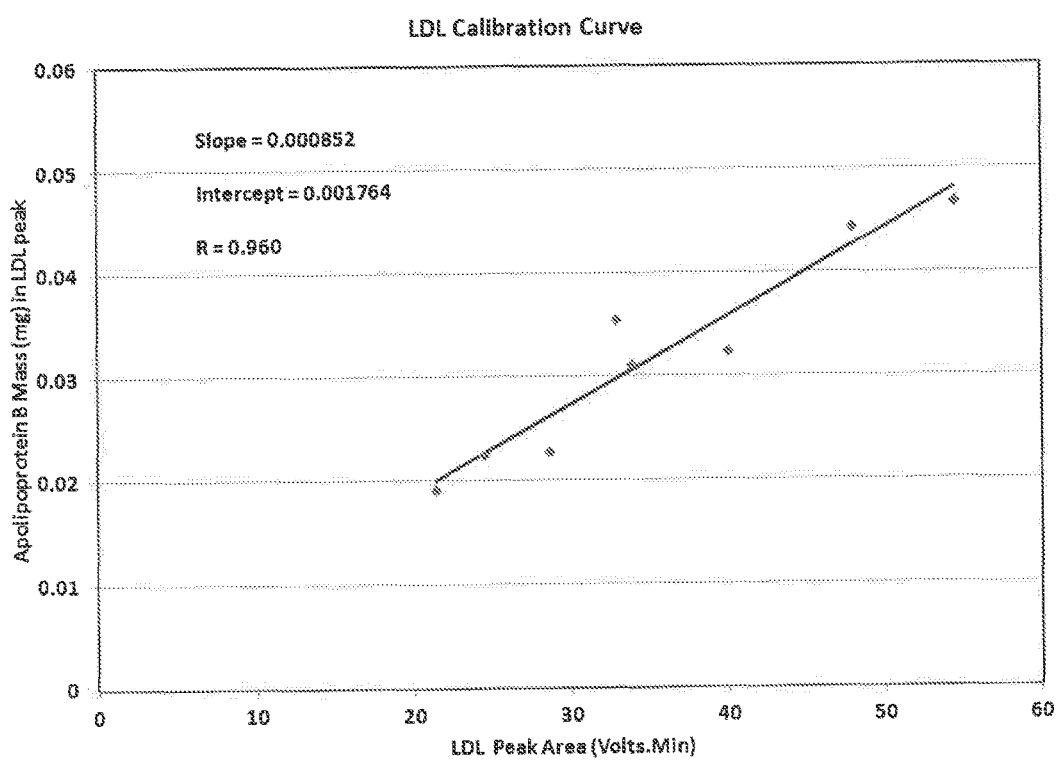
FIG. 2 shows an exemplary particle calibration curve for LDL.
Figure 3:
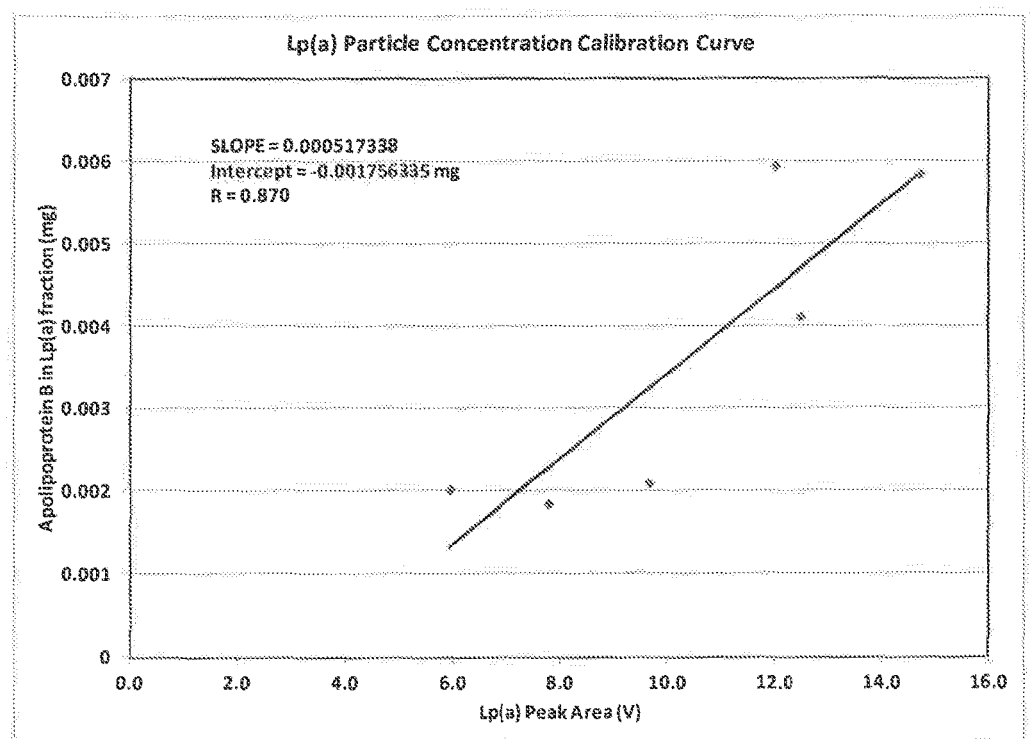
FIG. 3 shows an exemplary particle calibration curve for Lp(a).
Figure 4:
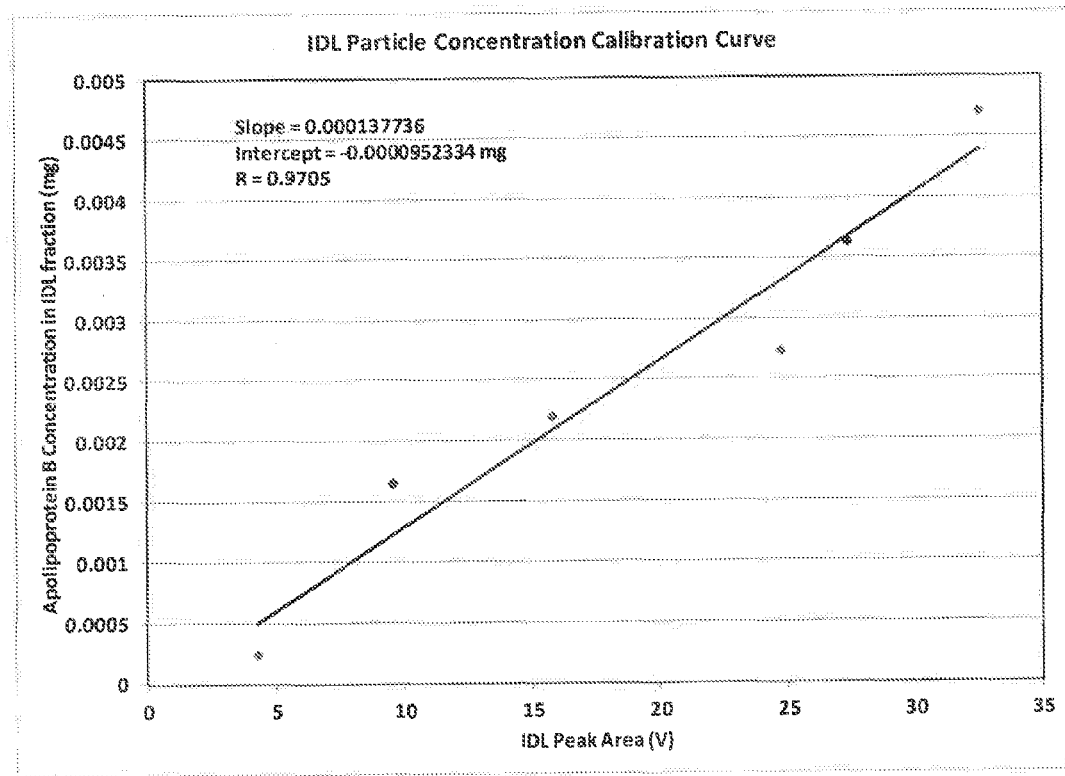
FIG. 4 shows an exemplary particle calibration curve for IDL.
Figure 5:
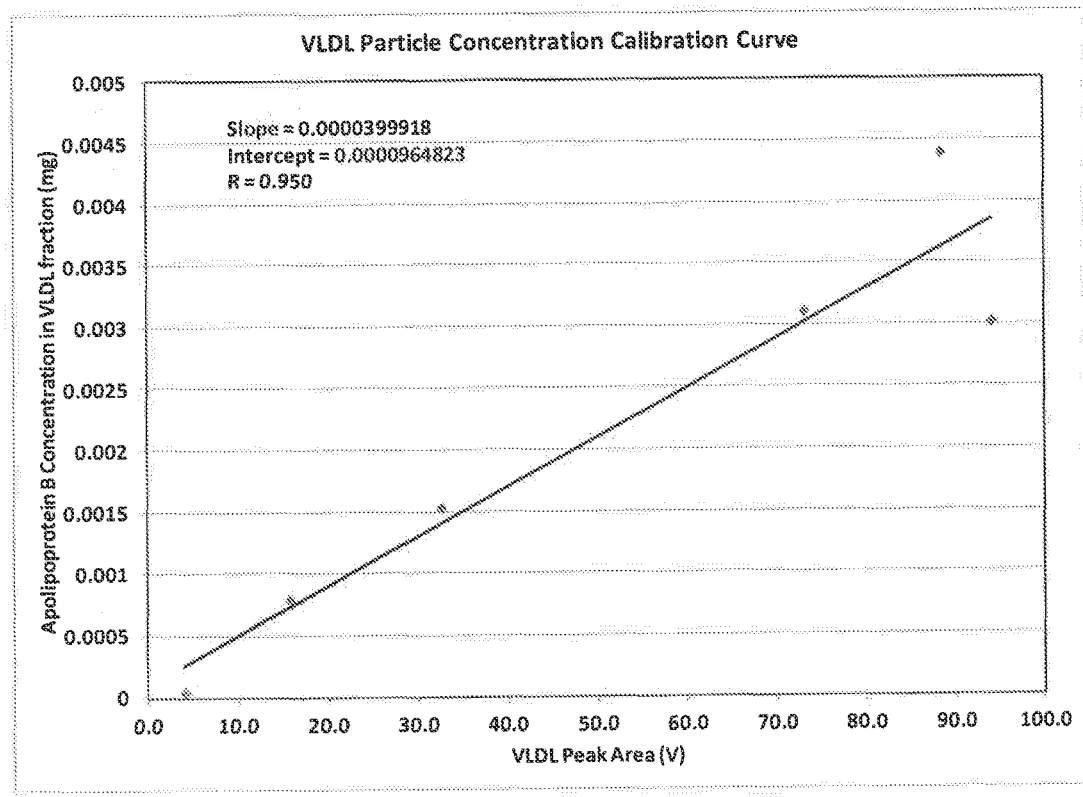
FIG. 5 shows an exemplary particle calibration curve for VLDL.

An example of calibration curve for LDL is shown in FIG. 2. Exemplary calibration curves for Lp(a), IDL and VLDL are shown in FIGS. 3-5. The peak area represents the volt-minutes under the peak obtained using a light scattering detector after the LDL fraction had been separated from the other serum components by density-gradient centrifugation. ApoB mass in the LDL fraction was determined by commercial immunoassay.

Once the amount of apo B in the LDL peak of an unknown sample is calculated from the calibration curve it can be converted to particle number (nmol/L) using equation 2:

$$Z_{LDL} = A/(V \times MW_{apoB}) \qquad \text{Equation 2}$$

$Z_{LDL}$ is the LDL particle number or concentration (nmol/L)
A=LDL apo B concentration in mg×$10^{12}$
V=actual serum volume used in μls
$MW_{apoB}$=molecular weight of apo B (550,000 Da)

Figure 6:
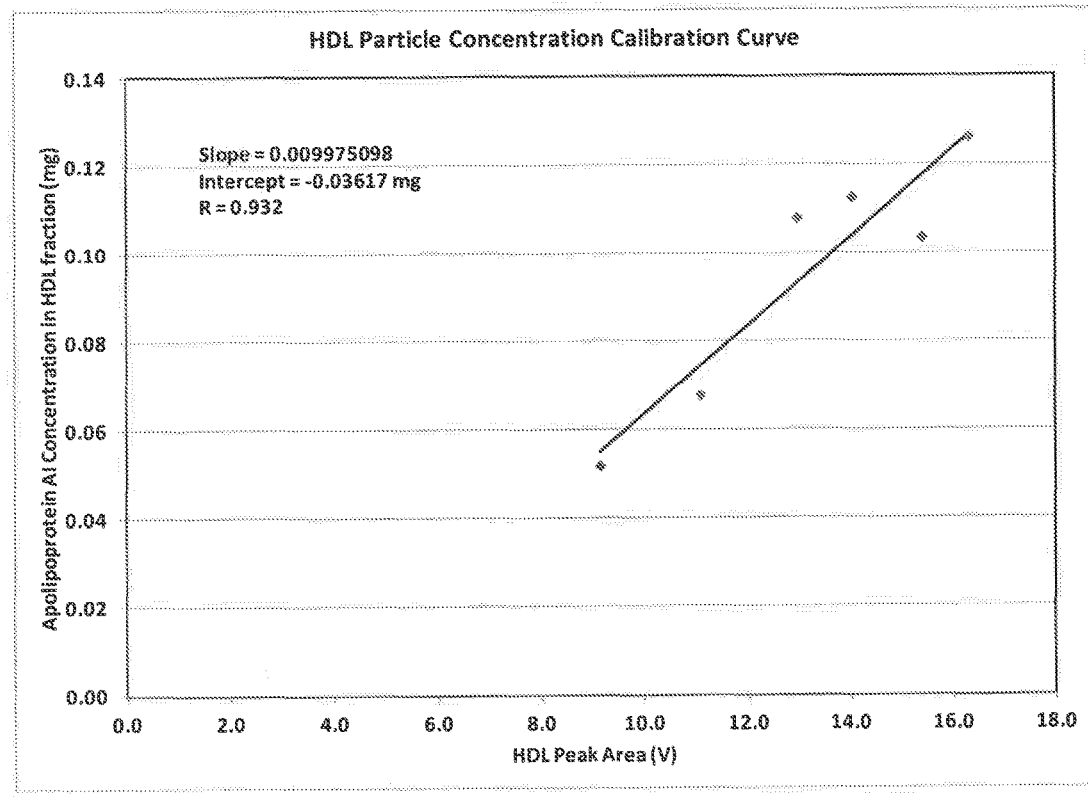
FIG. 6 shows an exemplary particle calibration curve for HDL.
Figure 7A:
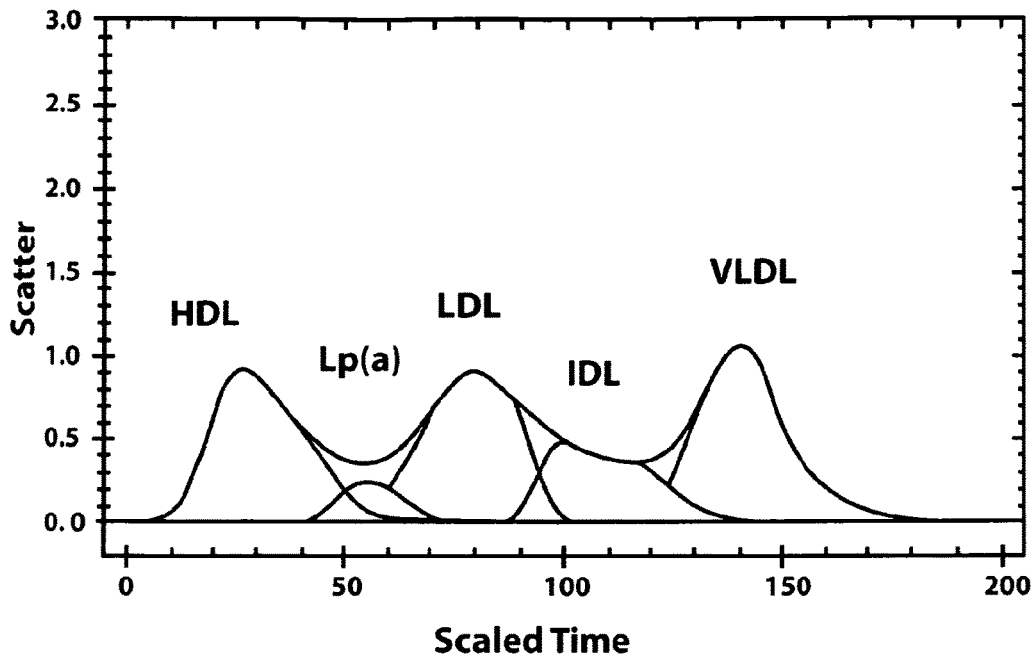
FIG. 7A shows a deconvoluted profile of a sample having a low triglyceride count (94 mg/dL) analyzed under the separation conditions referenced as Condition 2.
Figure 7B:
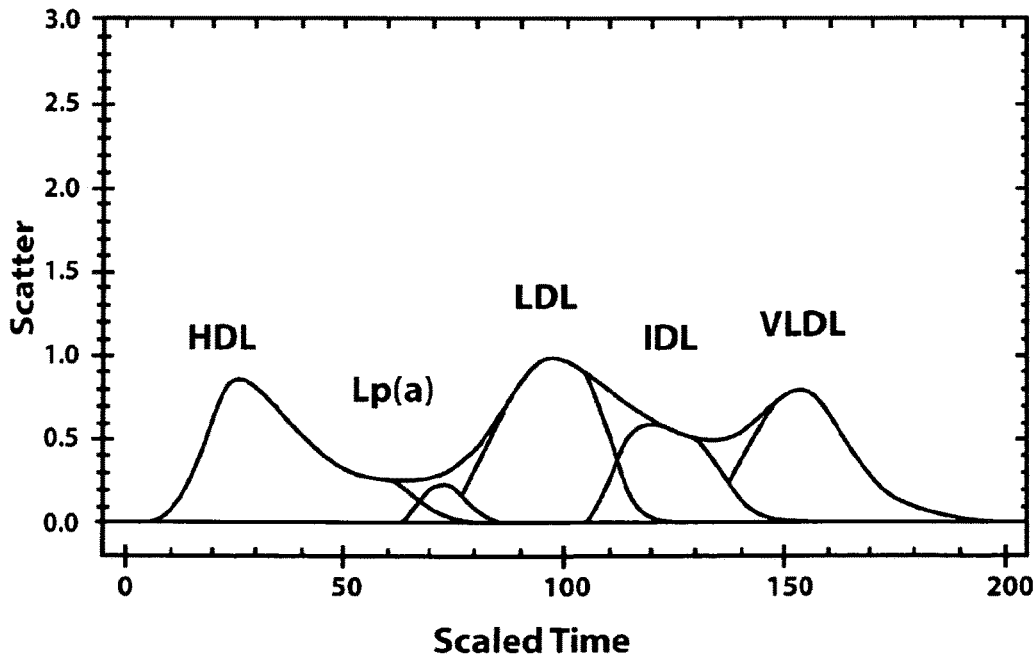
FIG. 7B shows a deconvoluted profile of a sample having a low triglyceride count (94 mg/dL) analyzed under the separation conditions referenced as Condition 1.
Figure 7C:
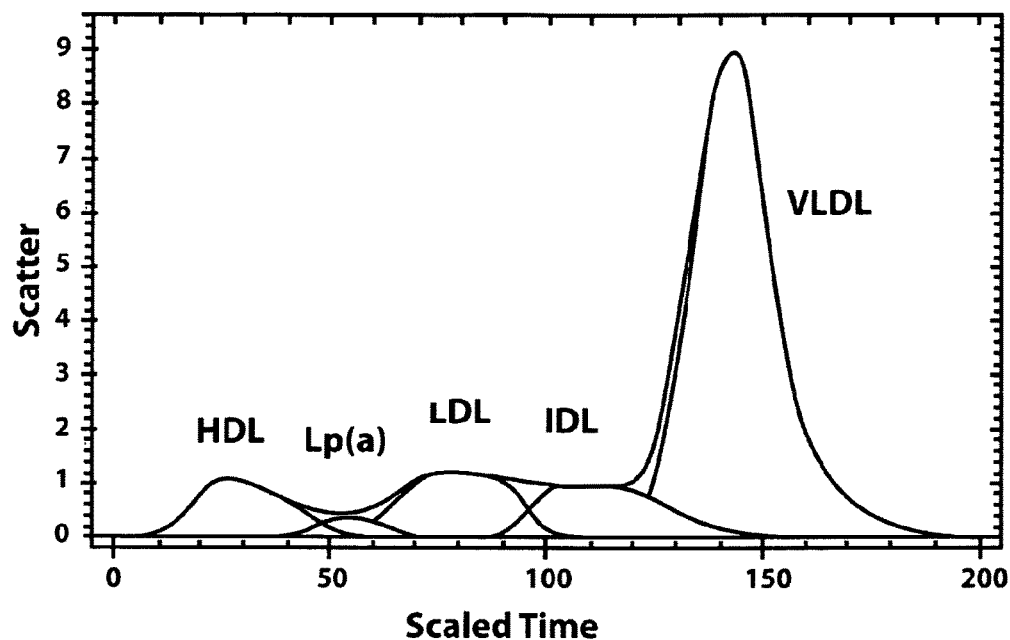
FIG. 7C shows a deconvoluted profile of a sample having a high triglyceride count (437 mg/dL) analyzed under the separation conditions referenced as Condition 2.
Figure 7D:
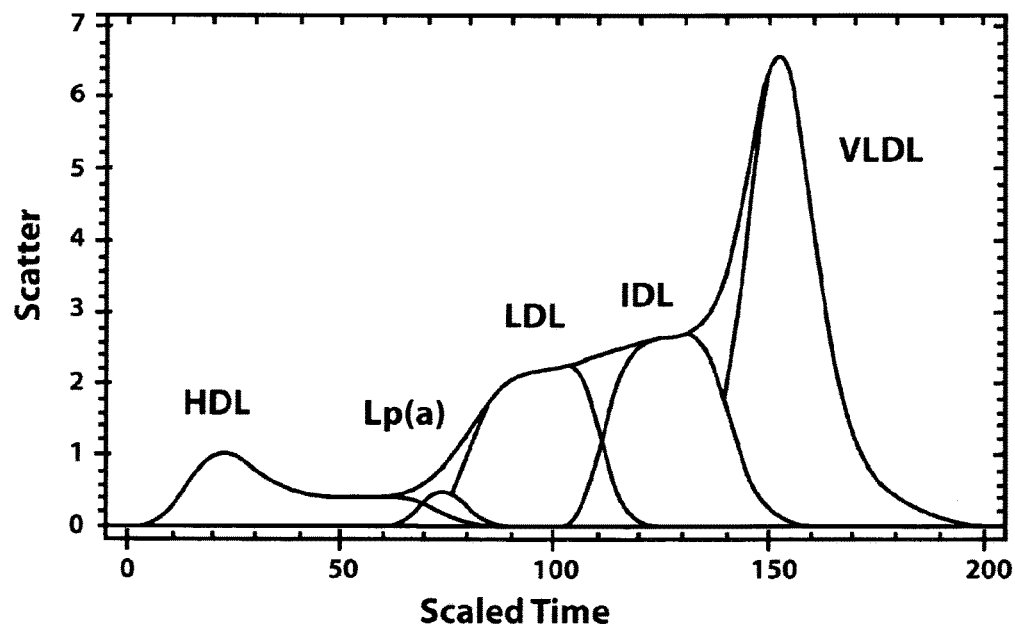
FIG. 7D shows a deconvoluted profile of a sample having a high triglyceride count (437 mg/dL) analyzed under the separation conditions referenced as Condition 1.

An additional specific example of the calibration procedure is provided using HDL. The process is carried out as described above, with the exception that apo AI is used as the marker. However, unlike the presence of a single apo B molecule on all atherogenic lipoproteins, such as LDL, IDL, VLDL, and Lp(a), the number of Apo AI molecules on HDL particle is known to vary from 2 to 5. Although there are methods available to measure the number of Apo AI molecules on HDL particle, for the sake of simplicity it is assumed that each HDL particle contains 3 molecules of Apo AI. An example of calibration curve for HDL is shown in FIG. 6. The peak area represents the volt-minutes under the peak obtained using a light scattering detector after the LDL fraction had been separated from the other serum components by density-gradient centrifugation. Apo AI mass in the HDL fraction was determined by commercial immunoassay.

In order to find apo B concentration in LDL of unknown sample, equation 1 is used as above, but the values of Y and x are as defined below.

Y is the HDL apo A1 concentration which is to be determined; and
x is the HDL peak area in V·min.

Once the amount of Apo AI in the HDL peak of an unknown sample is calculated from the calibration curve it can be converted to particle number (μmol/L) using equation 3:

$$Z_{HDL} = A/(V \times (3 \times MW_{ApoAI})) \qquad \text{Equation 3}$$

$Z_{HDL}$ is the HDL particle number or concentration (μmol/L)
A=HDL Apo AI concentration in mg×$10^{12}$
V=actual serum volume used in μls
$MW_{ApoAI}$=molecular weight of apo B (28,000 Da)

D. Methods of Measuring Lipoproteins

Methods of determining lipid particle number in a sample from a subject are provided. In one embodiment, the lipid is a lipoprotein. In another embodiment, the lipid is a lipoprotein selected from the group consisting of HDL, Lp(a), LDL, IDL and VLDL; the particle number for one or more of the lipoproteins may be determined. In one embodiment, the sample is a blood sample. In another aspect the sample is a blood serum sample. In one embodiment, light scattering measurements are employed as the photometric measurement.

A general embodiment of the method comprises obtaining a photometric measurement of a lipid fraction from a sample and calculating a particle count for the lipid fraction, where the particle count is a function of the photometric measurement. The method may further comprise separating a sample into a plurality of lipid fractions to facilitate the measurement. In one aspect of this embodiment, the lipid is a lipoprotein. In another embodiment, the lipid is a lipoprotein selected from the group consisting of HDL, Lp(a), LDL, IDL and VLDL; the particle number for one or more of the lipoproteins may be determined. In one aspect of this embodiment, a given lipid fraction contains only a single lipid species or predominately a single species of lipid, such as, for example, LDL. In one aspect, the photometric measurement is a measurement of light scattering caused by the lipid fraction. The sample may be fractioned, either completely or partially, prior to the photometric measurement being obtained.

Another general embodiment of the method comprises subjecting a sample from a subject containing a lipid to a fractionation technique, the fractionation technique resulting in a plurality of fractions, wherein at least one of the fractions contains a lipid. Such a fraction containing a lipid is referred to herein as a lipid fraction. A single sample may be fractionated into one, two, three or $n^{th}$ lipid fractions. Not every fraction separated need contain a lipid. Furthermore, in one aspect of this embodiment, a single fraction contains a single lipid or predominately a single lipid. In addition, in one aspect of this embodiment, a single fraction contains more than one lipid.

In one aspect of this embodiment, the method comprises separating a first lipid fraction in a sample, obtaining a photometric measurement of a lipid in the first lipid fraction and calculating a particle count for the lipid in the first lipid fraction, where the particle count is a function of the photometric measurement. Such a method may further comprise separating a second, third and $n^{th}$ lipid fraction in a sample, obtaining photometric measurement for at least one of the second, third and $n^{th}$ lipid fractions and calculating a particle count for at least one of the lipids contained in the second, third and $n^{th}$ lipid fractions, wherein the particle count is a function of the photometric measurement.

In another aspect of this embodiment, the lipid is a lipoprotein. In another embodiment, the lipid is a lipoprotein selected from the group consisting of LDL, Lp(a), LDL, IDL and VLDL; the particle number for one or more of the lipoproteins may be determined.

Therefore, in another general embodiment, the method comprises obtaining a measurement of light scattering of a lipid fraction from a subject and calculating a particle count for at least one lipid in the lipid fraction, where the particle count is a function of the measurement of light scattering. In one aspect of this embodiment, the lipid is a lipoprotein. In another embodiment, the lipid is a lipoprotein selected from the group consisting of LDL, Lp(a), LDL, IDL and VLDL; the particle number for one or more of the lipoproteins may be determined. In one aspect of this embodiment, the lipid fraction contains only a single lipid species, such as, for example, LDL. The lipid fraction may be fractioned, either completely or partially, prior to the photometric measurement being obtained.

Another general embodiment of the method comprises subjecting a sample from a subject containing a lipid to a fractionation technique, the fractionation technique resulting in a plurality of subdivisions of the sample, wherein at least one of the subdivisions contains a lipid. Such a subdivision containing a lipid is referred to herein as a lipid fraction. A single sample may be fractionated into one, two, three or $n^{th}$ lipid fractions. Not every fraction separated need contain a lipid.

In one aspect of this embodiment, the method comprises separating a first lipid fraction in a sample, obtaining a measurement of light scattering of a lipid in the first lipid fraction and calculating a particle count for the lipid in the first lipid fraction, where the particle count is a function of the measurement of light scattering. Such a method may further comprise separating a second, third and $n^{th}$ lipid fraction in a sample, obtaining a measurement of light scattering for at least one of the second, third and $n^{th}$ lipid fractions and calculating a particle count for at least one of the lipids contained in the second, third and $n^{th}$ lipid fractions, wherein the particle count is a function of the measurement of light scattering.

In another aspect of this embodiment, the lipid is a lipoprotein. In another embodiment, the lipid is a lipoprotein selected from the group consisting of LDL, Lp(a), LDL, IDL and VLDL; the particle number for one or more of the lipoproteins may be determined.

In a further aspect of this embodiment, one or more of the plurality of lipid fractions contain a lipoprotein. In still a further aspect, two or more, three or more, four or more or five or more of the lipid fractions contain a lipoprotein. One or more lipid fractions may contain the same lipoprotein and the fractions be considered together when determining the particle number for the lipoprotein. In one aspect, the fractions containing the same lipoprotein are considered together using a deconvolution algorithm as described herein. As discussed above, a single lipid fraction may contain a single lipoprotein. Furthermore, a single lipid fraction may contain substantially a single lipoprotein.

In the following discussion, the lipid is referred to herein as a lipoprotein for simplicity. The methods described herein may be used for other serum lipids as well.

In a particular embodiment of the foregoing methods, the lipoproteins in the first, second, third and/or $n^{th}$ lipid fractions may be separated based on density of the lipoprotein contained in each fraction.

In a further particular embodiment of the foregoing methods, the first, second, third and/or $n^{th}$ lipid fractions contain only a single species of lipoprotein or contain substantially only a single species of lipoprotein. The use of the term substantially as used herein with reference to a particular species of lipoproteins or other chemical entity means that the species of lipoprotein in a given fraction comprises 75% or more of the total lipoprotein present in the fraction (as measured on a weight to weight basis). In one embodiment, the species of lipoprotein in a given fraction comprises 85% or more of the total lipoprotein present in the fraction (as measured on a weight to weight basis). In another embodiment, the species of lipoprotein in a given fraction comprises 90% or more of the total lipoprotein present in the fraction (as measured on a weight to weight basis). In another embodiment, the species of lipoprotein in a given fraction comprises 95% or more of the total lipoprotein present in the fraction (as measured on a weight to weight basis). In another embodiment, the species of lipoprotein in a given fraction comprises 97% or more of the total lipoprotein present in the fraction (as measured on a weight to weight basis). In another embodiment, the species of lipoprotein in a given fraction comprises 98% or more of the total lipoprotein present in the fraction (as measured on a weight to weight basis). In another embodiment, the species of lipoprotein in a given fraction comprises 99% or more of the total lipoprotein present in the fraction (as measured on a weight to weight basis).

In a particular embodiment of the foregoing methods, more than one of the first, second, third and or $n^{th}$ lipid fractions may each contain a single lipoprotein or substantially a single lipoprotein, such as, but not limited to, HDL, Lp(a), LDL, IDL and VLDL, and be considered together in the calculations described herein. For example, the $10^{th}$ to $13^{th}$ lipid fraction may each contain LDL or substantially contain LDL and be considered together in the calculations described herein for determining the particle number of LDL.

In a particular embodiment of the foregoing methods, the first, second, third and/or $n^{th}$ lipid fractions may contain more than one lipoprotein in such fractions, such as, but not limited to, HDL, Lp(a), LDL, IDL and VLDL, and each fraction containing such lipoprotein or substantially such lipoprotein may be considered together in the calculations described herein. For example, the $10^{th}$ to $13^{th}$ lipid fraction may each contain LDL or substantially contain LDL and be considered together in the calculations described herein for determining the particle number of LDL and the $14^{th}$ to $15^{th}$ lipid fractions may contain IDL or substantially contain IDL and be considered together in the calculations described herein for determining the particle number of IDL.

In another, example, the $2^{cd}$ to $5^{th}$ lipid fraction may each contain HDL or substantially contain HDL and be considered together in the calculations described herein for determining the particle number of HDL, the $10^{th}$ to $13^{th}$ lipid fraction may each contain LDL or substantially contain LDL and be considered together in the calculations described herein for determining the particle number of LDL and the $14^{th}$ to $15^{th}$ lipid fractions may contain IDL or substantially contain IDL and be considered together in the calculations described herein for determining the particle number of IDL.

In yet another example, the $2^{cd}$ to $5^{th}$ lipid fraction may each contain HDL or substantially contain HDL and be considered together in the calculations described herein for determining the particle number of HDL, the $7^{th}$ to $9^{th}$ lipid fraction may each contain Lp(a) or substantially contain Lp(a) and be considered together in the calculations described herein for determining the particle number of Lp(a), the $10^{th}$ to $13^{th}$ lipid fraction may each contain LDL or substantially contain LDL and be considered together in the calculations described herein for determining the particle number of LDL and the $14^{th}$ to $15^{th}$ lipid fractions may contain IDL or substantially contain IDL and be considered together in the calculations described herein for determining the particle number of IDL In yet another example, the $2^{cd}$ to $5^{th}$ lipid fraction may each contain HDL or substantially contain HDL and be considered together in the calculations described herein for determining the particle number of HDL, the $7^{th}$ to $9^{th}$ lipid fraction may each contain Lp(a) or substantially contain Lp(a) and be considered together in the calculations described herein for determining the particle number of Lp(a), the $10^{th}$ to $13^{th}$ lipid fraction may each contain LDL or substantially contain LDL and be considered together in the calculations described herein for determining the particle number of LDL, the $14^{th}$ to $15^{th}$ lipid fractions may contain IDL or substantially contain IDL and be considered together in the calculations described herein for determining the particle number of IDL and the $17^{th}$ to $18^{th}$ lipid fractions may contain VLDL or substantially contain VLDL and be considered together in the calculations described herein for determining the particle number of VLDL.

As used herein, when the term "fraction", "first lipid fraction", "lipid fraction", "lipoprotein fraction", "HDL fraction", "Lp(a) fraction", "LDL fraction", "IDL fraction", "VLDL fraction" or similar terms is used in the context of the methods described herein, the terms include the concept of adding together the amounts of a given lipoprotein class in more than one physical subdivision of the sample collected as a result of the fractionation technique. For example, the term "separating at least an LDL fraction in a sample" includes the concept of separating a sample into one or more physical fractions by a fractionation technique and adding together the LDL content in one or more of such subdivisions of the sample to determine the LDL fraction.

In a more particular embodiment of the method, the method comprises separating at least an LDL fraction in a sample, obtaining a measurement of the light scattering from the LDL fraction and calculating a particle count for the LDL fraction, wherein the particle count is a function of the measurement of light scattering. The method may further comprise separating at least one additional fraction in addition to an LDL fraction. Such additional fraction may include at least one of an HDL fraction, an Lp(a) fraction, an IDL fraction and a VLDL fraction. In one aspect, the additional fraction is an IDL fraction. In another aspect the additional fractions are an Lp(a) fraction and IDL fraction. In another aspect the additional fractions are an Lp(a) fraction, an IDL fraction and a VLDL fraction. In another aspect, the additional fractions are an HDL fraction, an Lp(a) fraction and an IDL fraction. In another aspect, the additional fractions are an HDL fraction, an IDL fraction and a VLDL fraction. In another aspect, the additional fractions are an HDL fraction, an Lp(a) fraction, an IDL fraction and a VLDL fraction. In another aspect, a particle count from only the LDL fraction is calculated.

In another more particular embodiment of the method, the method comprises separating at least an HDL fraction in a sample, obtaining a measurement of the light scattering from the HDL fraction and calculating a particle count for the HDL, fraction, wherein the particle count is a function of the measurement of light scattering. The method may further comprise separating at least one additional fraction in addition to an HDL fraction. Such additional fraction may include at least one of an Lp(a) fraction, a LDL fraction, an IDL fraction and a VLDL fraction. In one aspect, the additional fraction is an LDL fraction. In another aspect the additional fractions are an Lp(a) fraction and LDL fraction. In another aspect the additional fractions are an Lp(a) fraction, an LDL fraction and an IDL fraction. In another aspect, the additional fractions are an Lp(a) fraction, a LDL fraction, an IDL fraction and a VLDL fraction. In another aspect, a particle count from only the HDL fraction is calculated.

In another more particular embodiment of the method, the method comprises separating at least an Lp(a) fraction in a sample, obtaining a measurement of the light scattering from the Lp(a) fraction and calculating a particle count for the Lp(a) fraction, wherein the particle count is a function of the measurement of light scattering. The method may further comprise separating at least one additional fraction in addition to an Lp(a) fraction. Such additional fraction may include at least one of an HDL fraction, a LDL fraction, an IDL fraction and a VLDL fraction. In one aspect, the additional fraction is an LDL fraction. In another aspect the additional fractions are a HDL fraction and a LDL fraction. In another aspect the additional fractions are a HDL fraction, an LDL fraction and an IDL fraction. In another aspect, the additional fractions are a HDL fraction, a LDL fraction, an IDL fraction and a VLDL fraction. In another aspect, a particle count from only the Lp(a) fraction is calculated.

In a further more particular embodiment of the method, the method comprises separating at least an LDL fraction and an IDL fraction in a sample, obtaining a measurement of the light scattering from at least one of the LDL or IDL fractions and calculating a particle count for each of the fractions from which a light scattering measurement was obtained, wherein the particle count is a function of the measurement of light scattering. In one aspect of this embodiment, a light scattering measurement and a particle count are obtained for both the LDL and IDL fractions. In another aspect of this embodiment, a light scattering measurement and a particle count are obtained for only the LDL fraction or the IDL fraction. In another aspect of this embodiment, a light scattering measurement and a particle count are obtained for only the LDL fraction.

In a further more particular embodiment of the method, the method comprises separating at least a Lp(a) fraction, an LDL fraction and an IDL fraction in a sample, obtaining a measurement of the light scattering from at least one of the Lp(a), LDL and IDL fractions and calculating a particle count for each of the fractions from which a light scattering measurement was obtained, wherein the particle count is a function of the measurement of light scattering. In one aspect of this embodiment, a light scattering measurement and a particle count are obtained for each of the Lp(a), LDL and IDL fractions. In one aspect of this embodiment, a light scattering measurement and a particle count are obtained for each of the LDL and IDL fractions. In one aspect of this embodiment, a light scattering measurement and a particle count are obtained for each of the Lp(a) and LDL fractions. In another aspect of this embodiment, a light scattering measurement and a particle count are obtained for only the LDL fraction and the IDL fraction. In another aspect of this embodiment, a light scattering measurement and a particle count are obtained for only the LDL fraction.

In a further more particular embodiment of the method, the method comprises separating at least an LDL fraction, an IDL and a VLDL fraction in a sample, obtaining a measurement of the light scattering from at least one of the LDL, IDL and VLDL fractions and calculating a particle count for each of the fractions from which a light scattering measurement was obtained, wherein the particle count is a function of the measurement of light scattering. In one aspect of this embodiment, a light scattering measurement and a particle count are obtained for each of the LDL, IDL and VLDL fractions. In one aspect of this embodiment, a light scattering measurement and a particle count are obtained for each of the LDL and IDL fractions. In another aspect of this embodiment, a light scattering measurement and a particle count are obtained for only the LDL fraction and the IDL fraction. In another aspect of this embodiment, a light scattering measurement and a particle count are obtained for only the LDL fraction.

In a further more particular embodiment of the method, the method comprises separating at least an HDL fraction, an LDL fraction, an IDL and a VLDL fraction in a sample, obtaining a measurement of the light scattering from at least one of the HDL, LDL, IDL and VLDL fractions and calculating a particle count for each of the fractions from which a light scattering measurement was obtained, wherein the particle count is a function of the measurement of light scattering. In one aspect of this embodiment, a light scattering measurement and a particle count are obtained for each of the HDL, LDL, IDL and VLDL fractions. In one aspect of this embodiment, a light scattering measurement and a particle count are obtained for each of the LDL, IDL and VLDL fractions. In one aspect of this embodiment, a light scattering measurement and a particle count are obtained for each of the LDL and IDL fractions. In another aspect of this embodiment, a light scattering measurement and a particle count are obtained for only the HDL fraction, LDL fraction, the IDL fraction or the VLDL fraction. In another aspect of this embodiment, a light scattering measurement and a particle count are obtained for only the LDL fraction.

In a further more particular embodiment of the method, the method comprises separating at least an HDL fraction, an Lp(a) fraction, an LDL fraction, an IDL and a VLDL fraction in a sample, obtaining a measurement of the light scattering from at least one of the HDL, Lp(a), LDL, IDL and VLDL fractions and calculating a particle count for each of the fractions from which a light scattering measurement was obtained, wherein the particle count is a function of the measurement of light scattering. In one aspect of this embodiment, a light scattering measurement and a particle count are obtained for each of the HDL, Lp(a), LDL, IDL and VLDL fractions. In one aspect of this embodiment, a light scattering measurement and a particle count are obtained for each of the LDL, IDL and VLDL fractions. In one aspect of this embodiment, a light scattering measurement and a particle count are obtained for each of the LDL and IDL fractions. In another aspect of this embodiment, a light scattering measurement and a particle count are obtained for only the HDL fraction, LDL fraction, the IDL fraction or the VLDL fraction. In another aspect of this embodiment, a light scattering measurement and a particle count are obtained for only the LDL fraction.

In one aspect of the foregoing methods, a particle count is obtained for only the LDL fraction. In one aspect of the foregoing methods, a particle count is obtained for the LDL fraction and at least one additional fraction. Such additional fraction may be a HDL fraction, an Lp(a) fraction, an IDL fraction, a VLDL fraction or any combination of the foregoing. In one aspect of the foregoing methods, the additional fraction is an HDL fraction. In one aspect of the foregoing methods, the additional fraction is an Lp(a) fraction. In one aspect of the foregoing methods, the additional fraction is an IDL fraction. In one aspect of the foregoing methods, the additional fraction is a VLDL fraction. In one aspect of the foregoing methods, the additional fraction is an IDL fraction and an Lp(a) fraction. In one aspect of the foregoing methods, the additional fraction is a HDL fraction, an IDL fraction and an Lp(a) fraction. In one aspect of the foregoing methods, the additional fraction is a HDL fraction, an IDL fraction, an Lp(a) fraction and a VLDL fraction. In one aspect of the foregoing methods, the additional fraction is an IDL fraction, an Lp(a) fraction and a VLDL fraction.

In one aspect of the foregoing methods, a particle count is obtained for only the HDL fraction. In one aspect of the foregoing methods, a particle count is obtained for the HDL fraction and at least one additional fraction. Such additional fraction may be an Lp(a) fraction, an LDL fraction, an IDL fraction, a VLDL fraction or any combination of the foregoing. In one aspect of the foregoing methods, the additional fraction is an LDL fraction. In one aspect of the foregoing methods, the additional fraction is an Lp(a) fraction. In one aspect of the foregoing methods, the additional fraction is an IDL fraction. In one aspect of the foregoing methods, the additional fraction is a VLDL fraction. In one aspect of the foregoing methods, the additional fraction is an LDL fraction. In one aspect of the foregoing methods, the additional fraction is an Lp(a) fraction. In one aspect of the foregoing methods, the additional fraction is an Lp(a) fraction and an LDL fraction. In one aspect of the foregoing methods, the additional fraction is an Lp(a) fraction, an LDL fraction and an IDL fraction. In one aspect of the foregoing methods, the additional fraction is an Lp(a) fraction, an LDL fraction, an IDL fraction and a VLDL fraction.

In one aspect of the foregoing methods, a particle count is obtained for only the Lp(a) fraction. In one aspect of the foregoing methods, a particle count is obtained for the Lp(a) fraction and at least one additional fraction. Such additional fraction may be a HDL fraction, an LDL fraction, an IDL fraction, a VLDL fraction or any combination of the foregoing. In one aspect of the foregoing methods, the additional fraction is a HDL fraction. In one aspect of the foregoing methods, the additional fraction is an LDL fraction. In one aspect of the foregoing methods, the additional fraction is an IDL fraction. In one aspect of the foregoing methods, the additional fraction is a VLDL fraction. In one aspect of the foregoing methods, the additional fraction is an Lp(a) fraction and an LDL fraction. In one aspect of the foregoing methods, the additional fraction is an Lp(a) fraction, an LDL fraction and an IDL fraction. In one aspect of the foregoing methods, the additional fraction is an Lp(a) fraction an LDL fraction, an IDL fraction and a VLDL fraction.

In another embodiment of the method, only atherogenic lipoproteins are counted. Such an embodiment will comprise obtaining a measurement of light scattering from at least one atherogenic lipoprotein fraction and calculating a particle count for each of the atherogenic lipoprotein fractions from which a light scattering measurement was obtained, wherein the particle count is a function of the measurement of light scattering. The atherogenic lipoprotein in such fractions may be selected from the group consisting of: Lp(a), LDL, IDL, and VLDL. In a specific embodiment the atherogenic lipoprotein is LDL. In another specific embodiment the atherogenic lipoprotein is Lp(a). Lp(a) is known to being strongly predictive of cardiovascular disease, yet there are very few methods by which Lp(a) can be easily and accurately measured in serum samples.

The following is relevant to the methods described herein.

The subject may be any animal having lipoproteins to be measured. In the clinical setting the subject will often be a human patient, although it is conceivable that the subject will be a non-human animal in the veterinary setting. The subject may be human or non-human animal in the research setting. The animal in the research setting may be, for example, any commonly used model organism.

The lipid fraction from the subject will comprise a number of lipoproteins, such as an HDL, an Lp(a), an LDL, an IDL, and/or a VLDL. The various lipoproteins may be separated into at least one lipoprotein fractions as described herein. The lipoprotein fraction may be substantially pure such that it will be sufficiently free from other components that could affect the photometric measurement that a quantitative value for the lipoprotein in the lipid fraction can be obtained. Non-interfering components that do not affect the photometric measurement may be present. The fraction will not be completely free of interfering components in every embodiment. For example, there may be some amount of another lipoprotein fraction present. In a specific example, when lipoprotein fractions are fractionated on the basis of density, there may be overlap between adjacent lipoprotein fractions. For example, there may be Lp(a) present in the HDL fraction or there may be IDL present in the LDL fraction.

In some embodiments of the method, the lipid fraction consists essentially of serum components. In such embodiments the fraction contains no additional reagents, dyes, or other substances that may be added to facilitate measurement. This is possible in such embodiments because, unlike many other methods of quantifying serum lipids, including but not limited to lipoproteins, many embodiments of the photometric methods disclosed herein do not require the addition of reagents, dyes, fluorochromes, or the like. Any such artificially introduced substances that facilitate measurements are referred to herein as "analytical reagents." In some embodiments of the method the serum lipid fractions generated contains no substantial amount of analytical reagents, such that any analytical reagents present are present in sufficiently low concentrations that they do not affect the measurements. In other embodiments the lipoprotein fraction contains no analytical reagent.

E. Photometric Measurements

In the methods described herein, the particle count is calculated as a function of a photometric measurement. In some embodiment, the photometric measurement is light scattering. In some embodiments the function is approximately linear. In some embodiments the photometric measurement will be in the form of a curve, typically representing the relationship between run time and the readout of the detector. Characteristics of such curves generated from the photometric measurement include peak height and peak area; such characteristics may be used to calculate a particle number. Peak area is calculated in a variety of ways, most often simply by multiplying the peak height by half of the distance from trough to trough (as if the peak were a triangle). In certain embodiment, software is provided with measuring devices that automatically computes peak area. In cases in which two peaks are not completely resolved, "deconvolution" transformations may be performed to determine a poorly resolved peak area. Such methods involve taking the area of an aggregate peak and subtracting the contribution of one peak (generally the better resolved peak) to determine the area of the remaining peak.

Deconvolution is commonly used to resolve small peaks from larger adjacent peaks. In such cases often the smaller peak is only visible as a trough between two larger adjacent peaks, wherein the trough is not as deep as expected. The process comprises extrapolating the expected area under the trough between the larger peaks, subtracting the expected area of the trough from the actual area of the actual trough, wherein the difference in areas is the area under the smaller peak.

Examples of small lipoprotein peaks calculated by deconvolution are shown in FIGS. 8-11. The heavy black line shows actual light scattering values. The thinner lines show extrapolated peaks for each of the fractions (from left to right: HDL, Lp(a), LDL, IDL, and VLDL). The shaded peak is the IDL peak, calculated by deconvolution of the LDL and VLDL peaks. The peak marked with horizontal hash lines is the Lp(a) peak, calculated by deconvolution of the HDL and LDL peaks.

Light scattering has been discovered to effectively enumerate lipoprotein particles after separation of lipoprotein fractions and without the use of additional reagents or dyes. In a specific embodiment the photometric measurement is light scattering. Light scattering may be measured over any detection arc, for example 360°, 180°, 90°, or 45°. In a specific embodiment light scattering is measured over a 90° detection arc.

F. Light Scattering Measurements

Light scattering can be measured by various means known in the art. In a particular embodiment, light scattering is measured using a laser light scattering detector. The detector may be a fixed-angle detector or a multi-angle detector. For a lipoprotein particle of a given type, the amount of light scattering is approximately proportional to the number of particles per unit volume. Typically scattering is measured over a set are, for example 360°, 180°, 90°, or 45°. In a specific embodiment light scattering is measured over a 90° detection arc. The particle count is an approximately linear function of light scattering, although the functions may differ depending on which lipoprotein fraction is being measured. The function can be determined by the calibration methods described below.

It is foreseeable that in some instances a linear relationship between particle count and light scattering for a given fraction will be linear only over a certain range of concentrations, and that above and below that certain range the relationship will not be linear. In such cases, when there is an indication that the particle count is outside of the range in which the relationship is linear, the sample may be either concentrated or diluted to obtain a sample with a particle count in the linear range. The calculation of the particle count will then be corrected for the dilution or concentration of the sample.

Some embodiments of the method comprise measuring the light scattering of more than one lipoprotein fraction, such that the light scattering of the highest density fraction to be measured is measured before the others. In some such embodiments the light scattering of each fraction is measured in order of descending density. That is to say that the light scattering of the fractions would be measured in the following order, with the understanding that not all of the listed fractions need be measured: HDL, Lp(a), LDL, IDL and VLDL. As an illustrative example, if only LDL and VLDL are to be measured, LDL would be measured first, followed by VLDL. In a particular embodiment, the sample is prepared by density-gradient ultracentrifugation, and the sample is drained from the bottom of a tube used for such centrifugation such that the highest density fractions are collected first and sent to a light scattering counter.

Another embodiment of the method comprises measuring the particle count of a lipoprotein fraction of a sample in any of the apparatuses disclosed below.

G. Separation of Lipids

In a particular embodiment, vertical spin density gradient ultracentrifugation is used to separate lipid fractions in a sample. In one aspect, the lipid is a lipoprotein. However, any separation means known in the art may be used.

Using density gradient ultracentrifugation, the lipoprotein particles are separated in the following order (from the bottom of the density gradient to the top of the density gradient): HDL, Lp(a), LDL, IDL and VLDL. A variety of density gradient ultracentrifugation conditions may be used. The composition of the density gradient may impact the separation between various lipoprotein species. The following are illustrated by way of example only and should not be interpreted as limiting the scope of the separation techniques to density gradient ultracentrifugation or as limiting the conditions employed in density gradient ultracentrifugation to those conditions specified.

As discussed above, in some cases certain a given fraction may contain more than one type of serum lipoprotein. This phenomenon may be caused by several factors, including factors related to the concentration of the various lipoprotein particles in a sample, the separation technique, such as, but not limited to, density gradient ultracentrifugation, and the equipment used in the separation itself. As discussed herein, techniques can be used to correct for this overlap, when encountered. In addition, specific density gradient ultracentrifugation conditions may be employed to provide maximum resolution of the various lipoprotein classes (such as for example, LDL, IDL and VLDL or HDL and Lp(a)) or may be employed to provide maximum resolution of a single lipoprotein (such as HDL, Lp(a) and/or LDL).

In one embodiment, the density gradient ultracentrifugation conditions and parameters are varied to provide maximum resolution of each of the various lipoprotein classes. In another embodiment, the density gradient ultracentrifugation conditions and parameters are varied to provide maximum resolution of one or more specific lipoprotein classes. In still another embodiment, the density gradient ultracentrifugation conditions and parameters are varied to provide maximum resolution of HDL. In still another embodiment, the density gradient ultracentrifugation conditions and parameters are varied to provide maximum resolution of Lp(a). In still another embodiment, the density gradient ultracentrifugation conditions and parameters are varied to provide maximum resolution of LDL.

Conditions and parameters that may be varied include, but are not limited to, density of the layers comprising the density gradient, volume of the layers comprising the density gradient, centrifugation time settings, acceleration setting (impacting the time it takes for the centrifuge to reach a set RPM), deceleration settings (impacting the time it takes for the centrifuge to come to a stop from the set RPM at the end a specified time setting), speed of the centrifuge (measured in RPM) and temperature of the centrifugation run. The various parameters discussed above may be varied singly or in any combination desired.

In one embodiment, the density gradient comprises two layers of gradient material (referred to as a top and bottom layer). A commonly used density gradient material is KBr. Other commonly used density gradient materials include cesium chloride, sucrose, and colloidal silica particles coated with polyvinylpyrrolidone (such as the product sold as Percoll®). Any density gradient solution known in the art to create the required density range may be used. Centrifugation will be performed in an appropriate vessel, such as a centrifuge tube. A variety of suitable centrifuge tubes are commercially available, for example from Beckman-Coulter, of Brea, Calif. In a specific embodiment separation is achieved using a single spin.

In one aspect of this embodiment, the density of the bottom layer ranges from 1.10 to 1.40 g/ml, from 1.15 to 1.30 g/ml or from 1.15 to 1.25 g/ml and the density of the top layer ranges from 0.5 to 1.2 g/ml, from 1.0 to 1.15 g/ml or from 1.0 to 1.10 g/ml. In another aspect of this embodiment, the density of the bottom layer is 1.21 g/ml or 1.30 g/ml and the density of the top layer is 1.05 g/ml. Further, in one aspect of this embodiment, the volume of the bottom layer ranges from 0.2 to 4.0 ml, from 0.8 to 2.5 ml or from 1 to 2 ml and the volume of the top layer ranges from 1 to 4.8 ml, from 1.2 ml to 3.0 ml or from 3.0 to 4.0 ml. In another aspect of this embodiment, the volume of the bottom layer is 2.0 ml or 1.0 ml and the volume of the top layer is 2.90 ml or 3.9 ml. Further, in one aspect of this embodiment, the settings for the ultracentrifuge are varied as follow: (i) centrifugation time from 10 to 70 minutes (note that centrifugation time does not include the time required for deceleration of the centrifuge rotor), from 15 to 50 minutes or from 20 to 40 minutes; (ii) centrifugation speed from 50,000 RPM to 75,000 RPM or 60,000 to 70,000 RPM; and (iii) centrifugation temperature from 15 to 30 degrees Celsius or from 20 to 25 degrees Celsius. Furthermore, in one aspect of this embodiment, the acceleration and deceleration settings are selected provide appropriate acceleration and deceleration profiles in order to maximize the desired separation. In one aspect, the acceleration and/or deceleration phases of the spin are set to be slow in order to minimize vibrations that may occur during a quick acceleration and/or deceleration. In one aspect, the acceleration and/or deceleration phases of the spin are set to be fast in order to resolve a given class of lipoprotein; faster acceleration and/or deceleration settings may be used when the density/volume of one or more layers of the density gradient, particularly the bottom layer, is increased 1.25 g/ml or 1.0 ml, respectively. For example, using a Beckman Coulter ultracentrifuge (Optima™ XL-100 K Ultracentrifuge), the acceleration and/or deceleration settings may range from 5 to 9 or 8 to 9 (with 9 being the slowest setting). In another aspect of this embodiment, the acceleration and/or deceleration settings may range from 1 to 5 or 2 to 4 (with 1 being the fastest setting.

In one embodiment applicable for general separation of lipoproteins from a sample, the following conditions are used.

| Condition 1 | |
|---|---|
| Bottom Layer KBr Density | 1.21 g/mL |
| Top Layer KBr Density | 1.004 g/mL |
| Bottom Layer Volume | 1.426 mL |
| Top Layer Volume | 3.56 mL |
| Centrifugation Time Setting | 36 minutes |
| Acceleration Settings | 6 |
| Deceleration Settings | 6 |
| Centrifugation Speed | 65000 rpm |
| Centrifugation Temperature | 23° C. |

In one aspect of this embodiment, the foregoing settings are used when the sample has a triglyceride concentration of less than 150 mg/dL.

As discussed herein, under certain conditions more than one type of lipoprotein may be present in a particular fraction. As a result, specific ultracentrifugation conditions may be used to maximize separation of a specific lipoprotein from one or more other lipoproteins.

In a particular embodiment, the density gradient ultracentrifugation conditions are used to provide maximum resolution of LDL and IDL lipoproteins. In addition, the methods for determining particle count employ obtaining a photometric measurement of a lipoprotein and determining a particle count based on the photometric measurement. When light scattering is used as the photometric measurements, certain lipoprotein particle may provide a greater readout (or signal) when compared to another lipoprotein particle. As a result, the readout for equal numbers of lipoprotein particles may be greater for one lipoprotein particle than for another. The applicants have discovered that under certain conditions, IDL lipoprotein may be present in one or more fractions where LDL lipoprotein is present. In addition, IDL lipoprotein particle have several-fold greater light scattering properties than LDL lipoprotein particles. As a result, any IDL lipoprotein particles in a LDL fraction may lead to overestimation of the LDL particle number. Such mixing of IDL and LDL lipoprotein particles may occur when the IDL lipoprotein particle concentration in a sample is elevated. The applicants have further found that IDL lipoprotein particle concentrations are generally elevated when triglyceride concentrations are over 150 mg/dL. Therefore, alternate conditions for separation may be required when IDL particle concentrations are elevated (such as, but not limited to, when triglyceride concentrations are over 150 mg/dL). In one embodiment, the following centrifugations conditions are used when triglyceride concentrations are over 150 mg/dL.

| Condition 2 | |
|---|---|
| Bottom Layer KBr Density | 1.21 g/mL |
| Top Layer KBr Density | 1.05 g/mL |
| Bottom Layer Volume | 1.0 mL |
| Top Layer Volume | 3.94 mL |
| Centrifugation Time Setting | 20 minutes |
| Acceleration Settings | 9 |
| Deceleration Settings | 9 |
| Centrifugation Speed | 65000 rpm |
| Centrifugation Temperature | 23° C. |

To illustrate the use of two specific centrifugation conditions discussed above, the two conditions were compared for situations where the triglyceride concentration was less than 150 mg/dL and greater than 150 mg/dL (see FIG. 7A-D). In FIG. 7, panels 7A and 7B represent the situation where triglyceride levels are less than 150 mg/dL (specifically 94 mg/dL) and panels 7C and 7D represent the situation where triglyceride levels are greater than 150 mg/dL (specifically 437 mg/dL). Furthermore, panels 7B and 7D represent the use of the centrifugation conditions referenced as Condition 1 above and panels 7A and 7C represent the use of the centrifugation conditions referenced as Condition 2 above (optimized for samples with triglyceride levels over 150 mg/dL). Examination of FIG. 7-A-D shows that the use of the centrifugation conditions referenced as Condition 2 above maintains the separation of lipoprotein particle fractions as compared to the use of Condition 1 above and provides accurate particle counts of the various lipoprotein classes (compare panels 7A and 7B). The use of the centrifugations conditions referenced as Condition 2 (7A) above provided a LDL particle count of 1238 while the use of the centrifugations conditions referenced as Condition 1 (7B) above provided a LDL particle count of 1248. Furthermore, it is evident that the use of the centrifugation conditions referenced as Condition 2 above provides superior separation of the LDL and IDL lipoprotein particle fractions in the high triglyceride condition (compare panels 7C and 7D). The use of the centrifugations conditions referenced as Condition 2 (7C) above provided a LDL particle count of 1955 while the use of the centrifugations conditions referenced as Condition 1 (7D) above provided a LDL particle count of 3100, indicating that the centrifugation conditions referenced as Condition 1 above resulted in less than optimal separation of LDL and IDL lipoprotein particles when IDL lipoprotein particle concentration was high (such as when triglyceride concentrations are greater than 150 mg/dL).

In a particular embodiment, the density gradient ultracentrifugation conditions are used to provide maximum resolution of HDL lipoproteins. In one embodiment, the following centrifugations conditions are used to provide maximal separation of HDL lipoproteins.

| Condition 3 | |
|---|---|
| Bottom Layer KBr Density | 1.30 g/mL |
| Top Layer KBr Density | 1.05 g/mL |
| Bottom Layer Volume | 2.0 mL |
| Top Layer Volume | 2.90 mL |
| Centrifugation Time Setting | 35 minutes |
| Acceleration Settings | 2 |
| Deceleration Settings | 2 |
| Centrifugation Speed | 65000 rpm |
| Centrifugation Temperature | 23° C. |

Figure 8A:
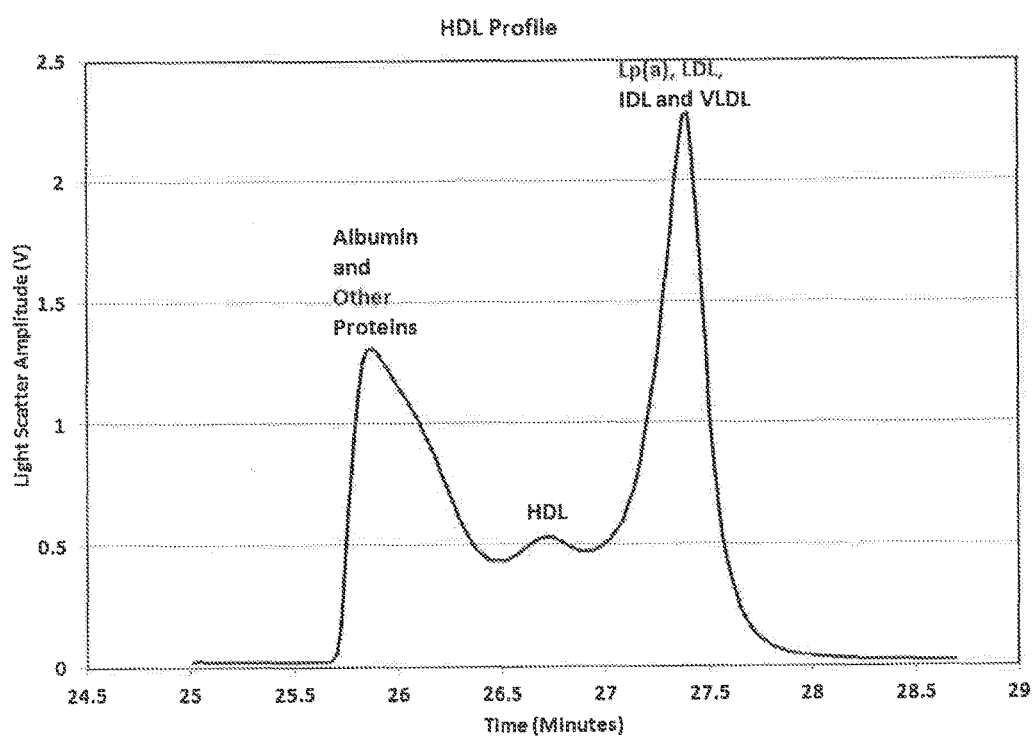
FIG. 8A shows a particle concentration profile collected with a light scattering detector illustrating a profile run under separation Condition 3 for resolution of HDL.
Figure 8B:
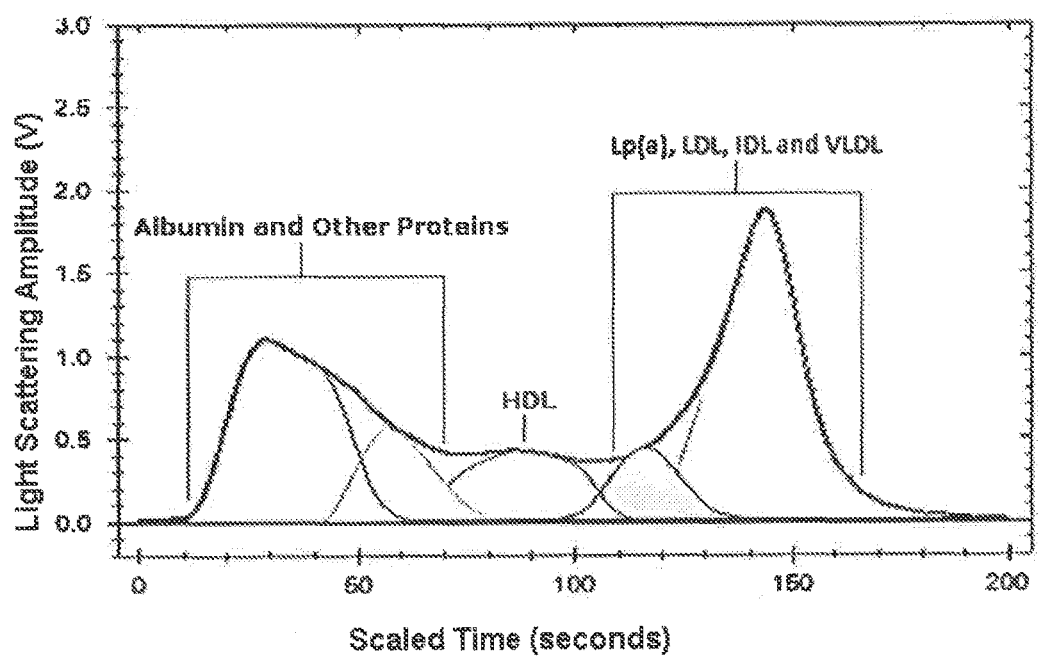
FIG. 8B shows the deconvoluted profile corresponding to the particle concentration profile shown in FIG. 8A.

The results of using the centrifugation conditions described as Condition 3 are shown in FIGS. 8A and 8B. FIG. 8A shows the concentration profile collected with a light scattering detector and FIG. 8B shows the corresponding deconvoluted profile. As can be seen in FIG. 8B, the HDL peak is well resolved. Furthermore, when compared to the profile shown in FIG. 7B (using Condition 1 described above), the HDL peak is shifted to the right and an additional peak consisting of albumin and other proteins is resolved from the HDL peak. The Lp(a), LDL, IDL and VLDL peaks are all compressed into a single peak to the far right of the profile.

In another particular embodiment, the density gradient ultracentrifugation conditions are used to provide maximum resolution of Lp(a) lipoproteins. In one embodiment, the following centrifugations conditions are used to provide maximal separation of Lp(a) lipoproteins.

| Condition 4 | |
|---|---|
| Bottom Layer KBr Density | 1.21 g/mL |
| Top Layer KBr Density | 1.05 g/mL |
| Bottom Layer Volume | 1.0 mL |
| Top Layer Volume | 3.94 mL |
| Centrifugation Time Setting | 40 minutes |
| Acceleration Settings | 9 |
| Deceleration Settings | 9 |
| Centrifugation Speed | 65000 rpm |
| Centrifugation Temperature | 23° C. |

Figure 9A:
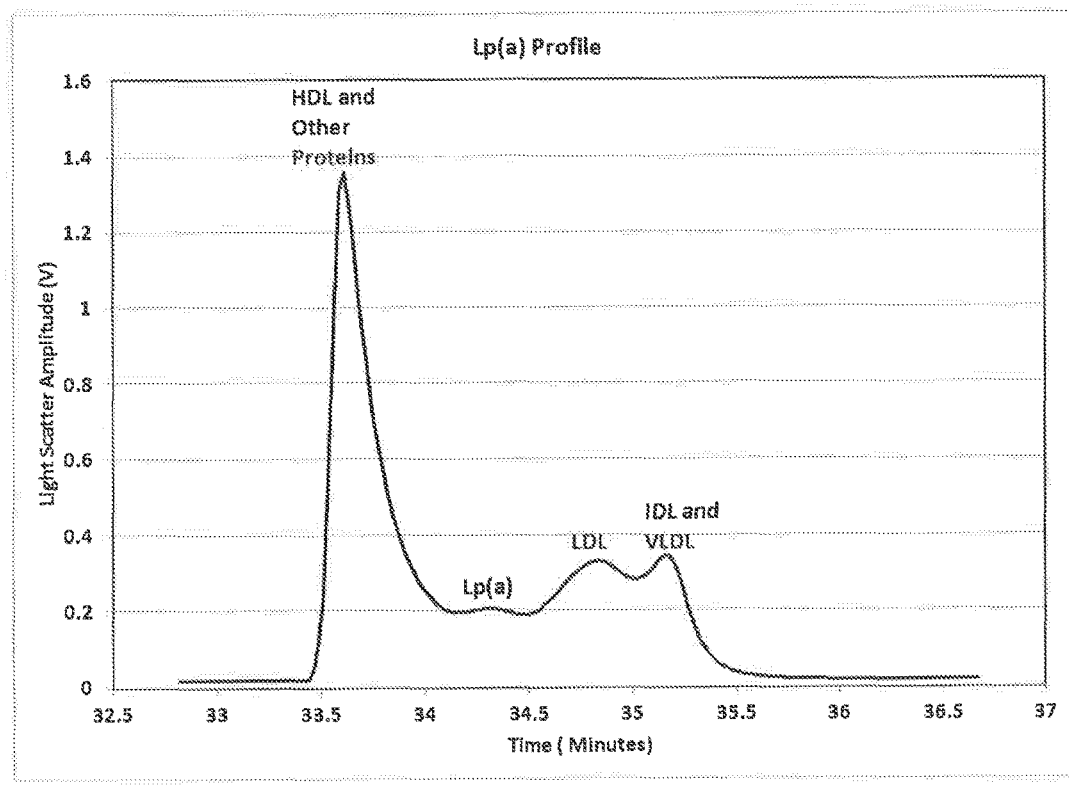
FIG. 9A shows a particle concentration profile collected with a light scattering detector illustrating a profile run under separation Condition 4 for resolution of Lp(a).
Figure 9B:
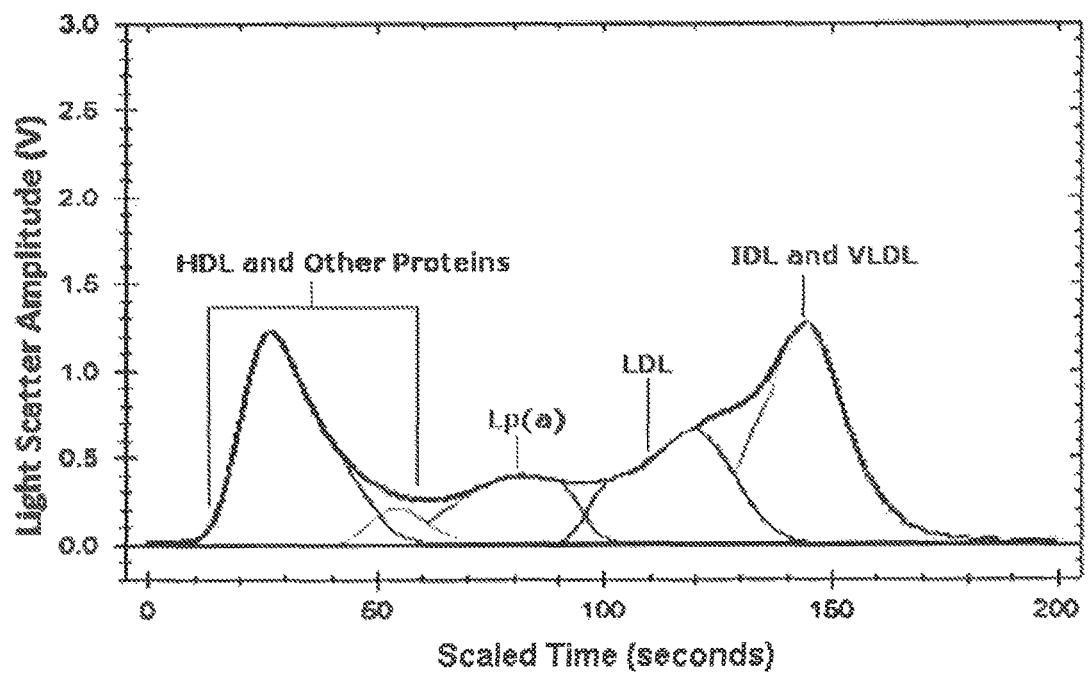
FIG. 9B shows the deconvoluted profile corresponding to the particle concentration profile shown in FIG. 9A.

The results of using the centrifugation conditions described as Condition 4 are shown in FIGS. 9A and 9B. FIG. 9A shows the concentration profile collected with a light scattering detector and FIG. 9B shows the corresponding deconvoluted profile. As can be seen in FIG. 9B, the Lp(a) peak is well resolved. Furthermore, when compared to the profile shown in FIG. 7B (using Condition 1 described above), the Lp(a) peak is shifted to the left providing separation from other lipoprotein particles.

H. Apparatus for Quantifying Lipoproteins

An apparatus is provided for quantifying lipoprotein particles in a plurality of serum lipid fractions. The apparatus generally functions by collecting lipoprotein fractions from a sample one fraction at a time and transporting each fraction to a light scattering counter. The counter then measures the scattered light, which can be used to calculate the particle count for the fraction.

A general embodiment of the apparatus comprises: a liquid conduit positioned to collect a sample from a sample vessel; and a light scattering counter positioned to receive the sample from the conduit. In one embodiment, the sample is collected from the bottom of the sample vessel.

The sample vessel may be any sample container known in the art. In some embodiments of the apparatus the sample vessel is a centrifuge tube. The use of a centrifuge tube has the advantage of using the same vessel for separation and for sampling. The centrifuge tube may have a bottom surface that is easily pierced by a sampler. In such embodiments a septum may be present on the bottom surface or the bottom surface may be a relatively thin structure.

The liquid conduit may be any structure suitable for conveying the liquid in the sample to the light scattering counter. Examples of such structures include pipes, tubes, channels, hoses, or any other conduit suitable for carrying liquid as known in the art. In a specific embodiment, the conduit is 8 mm (internal diameter) Teflon tubing. In one embodiment, the liquid conduit will be positioned to collect the sample from the bottom of the vessel. This allows the collection of vertically stratified layers, as will occur when lipoprotein fractions are separated by density-gradient centrifugation. Some embodiments of the liquid conduit comprise a sampler connected to the conduit to facilitate collection of the sample. In a specific embodiment the liquid conduit is connected to a sampling needle. The sampling needle may be positioned to penetrate the sample vessel to as to allow the liquid from the sample vessel to flow through the needle into the conduit. The diameter of the tubing may be varied to obtain a suitable flow rate of sample; the length of the tubing and the relative elevation of the sample vessel and the counter will also affect the flow rate, as is understood by those skilled in the art. All of these factors may be varied as needed.

The light scattering counter may be any suitable instrument, for example a laser light scattering counter. It may be configured to measure scattered light across any arc, as described above. The counter may comprise a flow cell, in which case the conduit may be connected to the flow cell so as to allow the liquid from the sample vessel to enter the flow cell wherein its light scattering properties will be measured.

The apparatus may further comprise a pump configured to pump the sample through the conduit to the counter. Various types of pumps may be used. In a specific embodiment the pump is a piston pump, which allows good control over the flow rate of the liquid.

The apparatus may comprise a sensor proximate to the conduit, wherein the sensor measures a fluid property within the conduit, and wherein said fluid property significantly differs in air and in liquid. The sensor is thus capable of distinguishing air from liquid in the conduit. Properties that can be used to distinguish air from liquid are well known in the art, and include thermal conductivity, electrical resistance, optical absorbance, and optical diffraction. Sensors capable of measuring these properties are well known in the art.

If air is detected in the conduit it might indicate that an entire sample has been taken, and that the sample vessel is now empty. In one embodiment, the sensor transmits a signal to indicate the presence of air in the conduit. In one embodiment, the sensor may send a signal to the pump to cease drawing fluid from the sample vessel when air is detected in the conduit. In some embodiments of the apparatus the sensor is connected to transmit a signal to a valve positioned on the conduit. In such embodiments the sensor may send a signal to close the valve when air is detected in the conduit.

The apparatus may further comprise a data logger connected to the counter. The data logger may record the data either digitally or graphically (i.e., on a paper printout). In embodiments in which the data are recorded on computer-readable media, the data may be further processed by a computing device. In some such embodiments the particle count for the lipoprotein fractions is computed by the computing device without direct human intervention. The resulting particle count may then be displayed or recorded. The term "computer-readable media" as used herein refers to a medium of storing information that is configured to be read by a machine. Such media include magnetic media, optical media, and paper media (punch cards, paper tape, etc.). Printed writing in a human language, if not intended or configured to be read by a machine, is not considered a computer-readable medium. In no case shall a human mind be construed as "computer-readable format."

The apparatus may also comprise a filter positioned on the conduit between the sample vessel and the counter. The filter functions to remove additional interfering particles. The pore size of the filter must be greater than the diameter of the lipoprotein to be counted. Ideally the pore size of the filter will be only slightly greater than the diameter of the lipoprotein to be counted, although it is to be understood that most classes of lipoprotein show a range of sizes. Filters with 100 nm pore size are quite suitable; they are readily available commercially and remove a significant amount of interfering serum components without removing lipoproteins. All lipoproteins, except chylomicrons, are less than 100 nm in diameter. Prefiltration may also be provided to remove larger particles to enhance the lifespan of a fine filter (such as the 100 nm fine filter described above); for example, a 2 μm pore-size filter will effectively remove larger particles.

The apparatus may comprise a reservoir of a cleaning fluid, such that the components of the apparatus may be flushed between samples. The cleaning fluid may be as simple as saline solution, de-ionized water, saline made from filtered de-ionized water, or any of these with the addition of detergents and surfactants. A specific embodiment of the cleaning fluid is a 40% v/v solution of Cleanz™ in water. The reservoir may be connected to a cleaning conduit that joins the main conduit between the valve and counter (downstream from the sensor and the sample vessel). The reservoir may be positioned above the components to be flushed to impart sufficient hydraulic head to cause the cleaning fluid to flow through the components under the force of gravity. A pump may be positioned to impart additional hydraulic head pressure to the cleaning fluid. While the valve is open the fluid will flush the end of the conduit positioned to collect the sample. While the valve is closed the fluid will flow through the conduit to the counter.

In one embodiment, the apparatus may be in communication with a control unit. The control unit is in communication with the various components of the apparatus and may receive input from such components and/or control the operation of such components. For example, the control unit may comprise the data logger, which as described above, receives the measurements of light scattering obtained from the light scattering counter. The control unit may contain executable programs to carry out functions associated with the methods described herein. For example, the control unit may comprise an executable file used to deconvolute the data generated. Furthermore, the control unit may comprise an executable file that generates a particle number from the light scattering data measured. In one aspect, the executable file is or contains an algorithm described herein. In one embodiment, the control unit is a general purpose computer. The general purpose computer may be programmed to carry out the functions described.

In another general embodiment, the apparatus comprises means for containing a liquid sample having vertically stratified fractions; means for conveying the lowest stratified fraction from the containing means; and means for counting particles configured to receive the lowest stratified fraction from the containing means by way of the conveying means. In some embodiments of the apparatus the means for counter particles are means for measuring light scattering. The apparatus may comprise means for flushing configured to flush the means for conveying and to flush the means for counting particles. The apparatus may also comprise means for sensing air within the conveying means.

Figure 10:
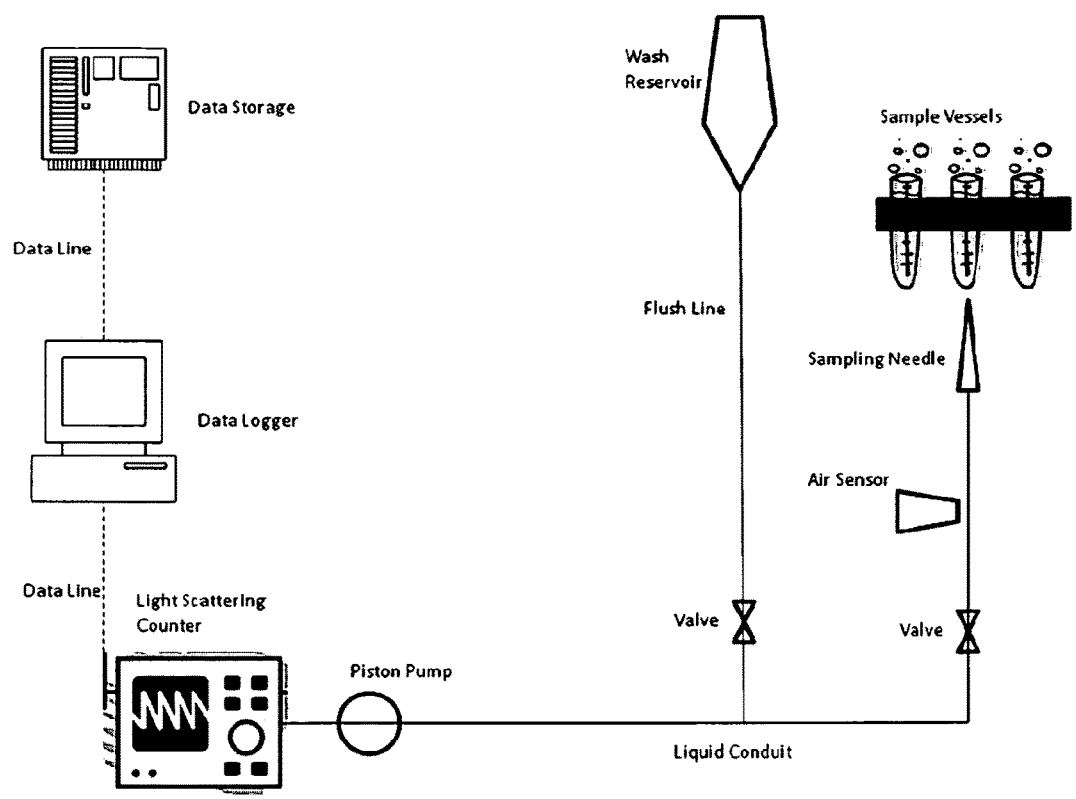
FIG. 10 shows a schematic illustration of one embodiment of the apparatus of the present disclosure.

Turning now to FIG. 10, an embodiment of the apparatus is presented comprising a sampling needle configured to puncture the bottom of a sample vessel; a tube having a first end and a second end, the first end connected to the sampling needle to receive a liquid sample from the needle; a light scattering counter connected to the second end of the tube and configured to measure light scattering in the sample when conveyed through the tube; an optical sensor positioned to measure the optical absorbance in the tube and capable of distinguishing air from liquid; a primary pump configured to pump the sample from the needle through the tube to the counter; a solenoid valve downstream of the sensor and connected to the sensor to receive an electrical signal causing the valve to close when air is detected by the sensor; and a flush reservoir connected to the tube.

I. Method of Calibration

Measurements of lipoprotein particle count may be calibrated by comparing the results of other methods of counting or determining the concentration of lipoprotein particles to photometric data. Apo B is particularly useful in this regard for the atherogenic lipoproteins (Lp(a), LDL, IDL, or VLDL), as there is only one molecule of apoB present in a given particle of each atherogenic lipoprotein. Apo AI is particularly useful in this regard for the HDL, as there are only 2-5 molecules of Apo AI present in a given particle of HDL; the exact number of Apo AI molecules may be determined for each HDL particle, or an average number of Apo AI molecules per HDL particle may be used in the calculations described.

A method for calibrating the measurement of a particle count of an lipoprotein is provided, the method comprising: (i) obtaining a photometric measurement of a lipoprotein from a calibration sample; (ii) measuring the molar concentration of specific marker, such as apoB for the atherogenic lipoproteins or Apo AI for HDL, in the lipoprotein fraction of the calibration sample; and (iii) calculating a regression between the photometric measurement and the molar concentration of the marker. The atherogenic lipoprotein may be selected from the group consisting of: Lp(a), IDL, LDL, and VLDL. The photometric measurement may be any disclosed above as suitable for determining the particle count of lipoproteins, including the measurement of light scattering. The regression may be an approximately linear regression, as would be expected between a measurement of light scattering and the particle count of a lipoprotein.

The molar concentration of apoB, apoA1 or other markers may be measured by various means known in the art. For example, commercially available immunoassays can be used to quickly and accurately measure the concentration of such markers in fractions containing lipoproteins from a sample. Such immunoassays may take any form in the art, including fluorescent, enzymatic and magnetic assays. One suitable assay is the Architect® system, available from Abbott Labs.

In many cases more than one calibration measurement will be necessary. Thus, the method may comprise obtaining a photometric measurement of the atherogenic lipoprotein from a second calibration sample; measuring the molar concentration of apoB in the second calibration sample; and calculating a regression based on the photometric measurement in the calibration sample, the molar concentration of apoB in the calibration sample, the photometric measurement in the second calibration sample, and the molar concentration of apoB in the second calibration sample. Additional measurements may be made as discussed above, as necessary to establish a sound regression.

J. Methods

The present disclosure also provides for a method of determining the risk of atherogenic disease in a subject, the method comprising quantifying at least one serum lipoprotein in a sample from the subject according to the methods disclosed herein and comparing the results with known correlations between the at least one serum lipoprotein concentration and the risk of atherogenic disease.

The method may further comprise obtaining a sample from the subject. Furthermore, the method may further comprise introducing the sample into an apparatus disclosed herein.

In one embodiment the serum lipoprotein is LDL. In another embodiment, the serum lipoprotein is HDL. In still another embodiment, the serum lipoprotein is Lp(a). In still another embodiment, the serum lipoprotein is IDL. In still another embodiment, the serum lipoprotein is VLDL. In still another embodiment, the serum lipoprotein is LDL and HDL. In still another embodiment, the serum lipoprotein is LDL and IDL. In still another embodiment, the serum lipoprotein is LDL, IDL and VLDL. In still another embodiment, the serum lipoprotein is LDL, IDL VLDL, HDL, and Lp(a).

K. Examples

Sample Collection and Separation

A blood sample is collected from the subject. Such a sample is collected as is known in the art, such as in a serum separator tube (SST) or plain red top serum tube. Serum is separated according to standard procedure and filtered to remove any clots, fibrin and any large interfering particles.

In one embodiment, samples are subject to density gradient centrifugation to separate lipid components. Density gradients were prepared using either manual pipette and dispensing devices or an automated liquid handler (such as the Tecan Genesis™). Multiple serum samples may be processed at one time. In one embodiment, a batch consisting of 16 serum samples is simultaneously prepared using an automated liquid handler. The following steps were used in the following examples:

1. Pipette 50 μL serum and mix with 1950 μL of 1.21 g/mL KBr solution.
2. Pipette 3.56 mL of 1.004 g/mL saline solution into a 5 mL Beckman centrifuge tube.
3. Slowly underlay 1.4256 ml of above prepared serum: KBr mixture to prepare a two density layer gradient.

Once the density gradient was prepared, all 16 centrifuge tubes with density gradients were placed in a Beckman Vertical Rotor (VTi 65) and centrifuged at 65,000 rpm for 47 minutes (including acceleration and deceleration) using a Beckman Coulter Optima XL 100 ultracentrifuge.

Apparatus

Particle concentration (in terms of moles of particles per unit volume) of separated lipoprotein classes and subclasses in the centrifugate were measured by using a working embodiment of the apparatus (referred to in this example simply as "the apparatus"). The apparatus is be an automated continuous flow through analysis system consisting of an automated specimen rack moving system, a tube piercing needle that can be automatically raised to pierce the tube, an end of sample drain detector, a sample valve that closes and opens automatically as programmed to facilitate the flow of sample from centrifuge tube, a piston pump to drain the sample from the centrifuge tube at a predetermined flow rate, a programmed pneumatic valve that allows the flow of baseline solution when sample is not flowing, a narrow bore (0.8 mm internal diameter) Teflon® tubing of a predetermined length (25 inches) that connects the pump to the multi-angle laser light scattering flow through detector (Wyatt Technology, Santa Barbara, Calif.) which outputs a light scattering signal proportional to the concentration of lipoprotein particles flowing through, an in line filter containing a 100 nm pore-size filter to remove interfering blood components placed between pump and detector, and software (ASTRA) that continuously collects the digital signal from the detector as sample flows through the detector. The sample is run at a flow rate of 3 mL per minute, using 25 inches of 0.8 mm Teflon™ tubing (resulting in a drain time of 1 minute 45 seconds). As the separated lipoprotein particles flow through the flow cell of the detector a laser impinges on the particles. As a result, they scatter light at various angles. The Wyatt instrument (DAWN HELEOS II) has 18 detectors (photodiodes) placed around the flow cell which collect signal from scattered light at their respective angles. The intensity of light is proportional to the type and number of lipoprotein particles flowing through. The signal is measured coming out of the detector placed at 90°. The method does not require any reagent, as it depends upon the physical phenomenon of light scattering. Such embodiments of the method simplify the instrumentation as well as reduce the cost of analysis.

Analysis and Exemplary Results

As the separated lipoprotein particles (all lipoprotein particles are separated based upon their density during ultracentrifugation with high density lipoprotein separating at the bottom of the centrifuge tube low density lipoprotein in the middle and very low density lipoprotein at the top) pass through the detector continuously during the draining of contents of centrifuge tube a continuous signal is obtained which consists of light scattering intensity peaks that correspond to respective lipoprotein classes as shown in FIGS. 11-14. The area of each peak is proportional to the respective number of particles of that lipoprotein per unit volume. Since the single vertical spin density gradient ultracentrifugation does not provide fully resolved (base line separated) peaks, deconvolution of the main continuous signal output curve into its component peaks corresponding to different lipoprotein peaks as more fully explained above.

Figure 11:
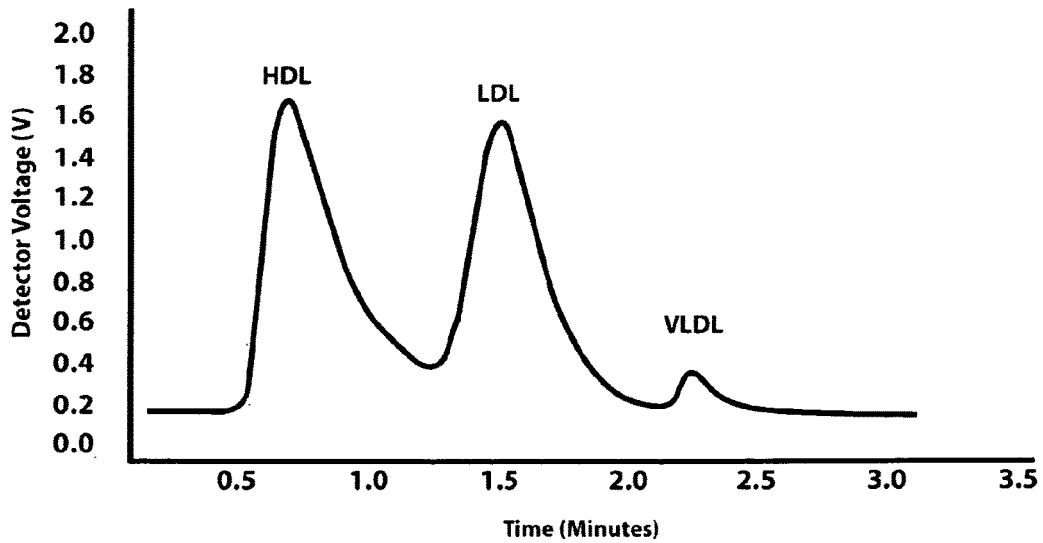
FIG. 11 shows an exemplary particle concentration profile collected with a light scattering detector showing a normal lipid profile with three well-resolved peaks for the HDL, LDL, and VLDL fractions.
Figure 12:
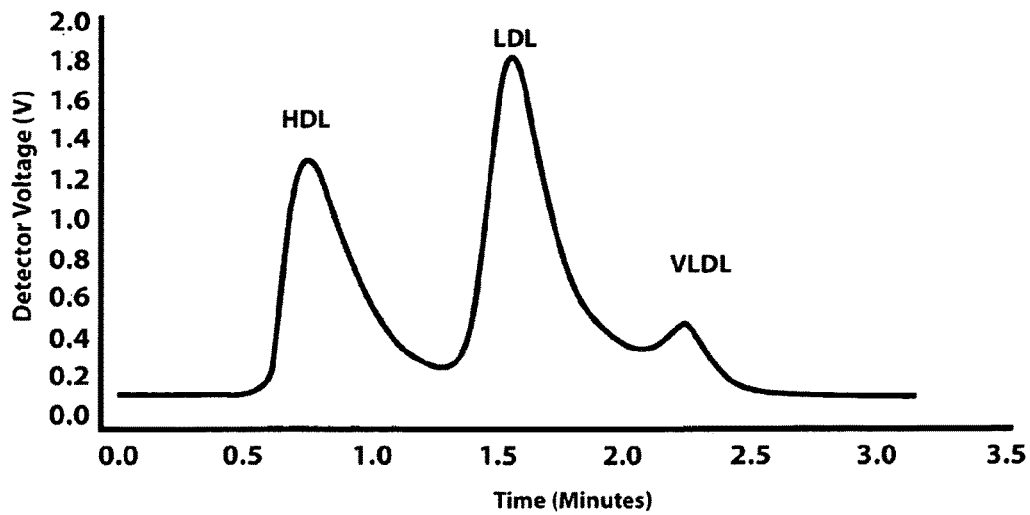
FIG. 12 shows an exemplary particle concentration profile collected with a light scattering detector showing a profile with a high LDL lipid profile with three well-resolved peaks for the HDL, LDL, and VLDL fractions.
Figure 13:
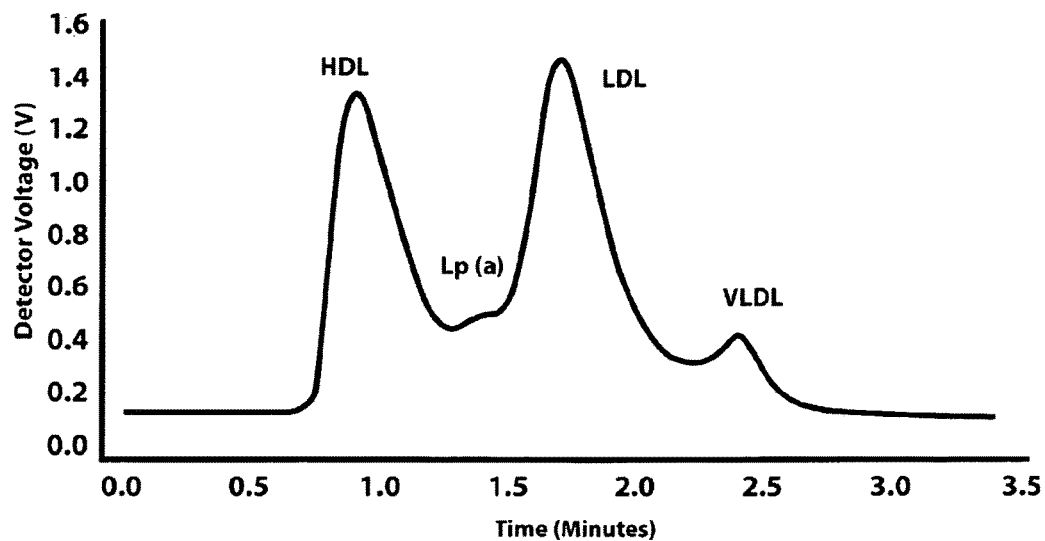
FIG. 13 shows an exemplary particle concentration profile collected with a light scattering detector showing a profile with a high Lp(a) lipid profile in which the Lp(a) peak falls between the HDL peak and LDL peak.
Figure 14:
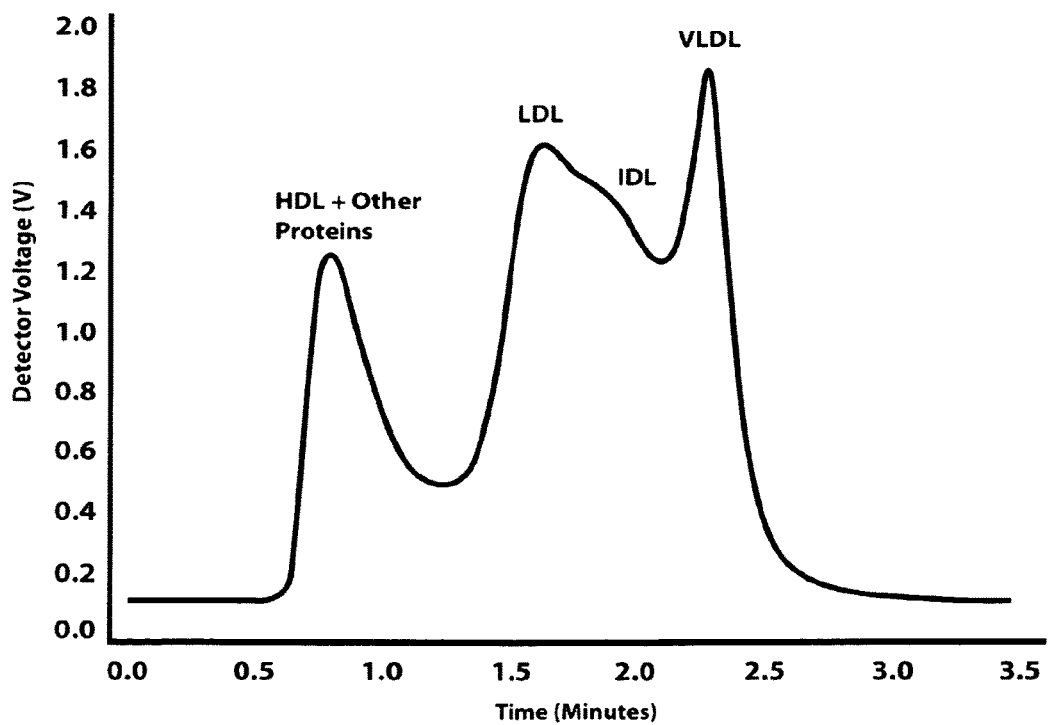
FIG. 14 shows an exemplary particle concentration profile collected with a light scattering detector showing a profile with a high IDL lipid profile in which the IDL peak falls between the LDL peak and VLDL peak.
Figure 15:
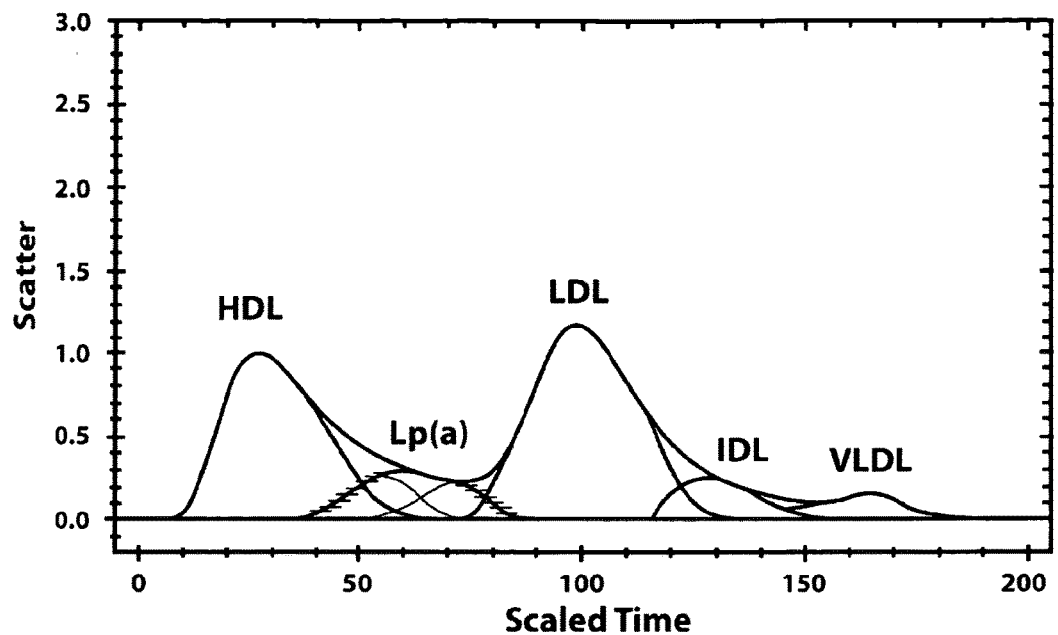
FIG. 15 shows the deconvoluted profile corresponding to the particle concentration profile shown in FIG. 11.
Figure 16:
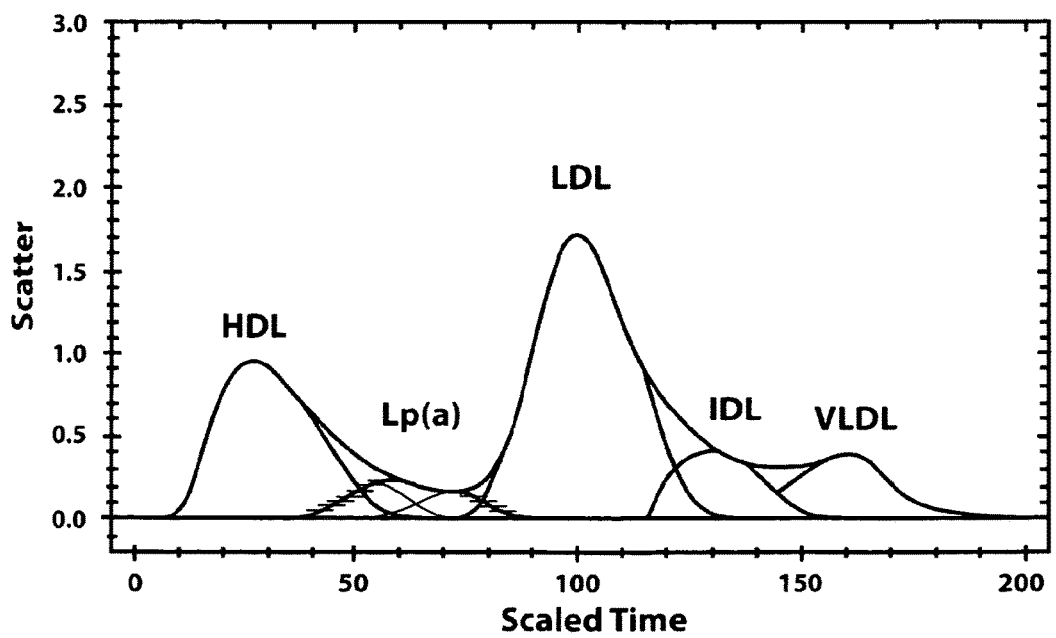
FIG. 16 shows the deconvoluted profile corresponding to the particle concentration profile shown in FIG. 12.
Figure 17:
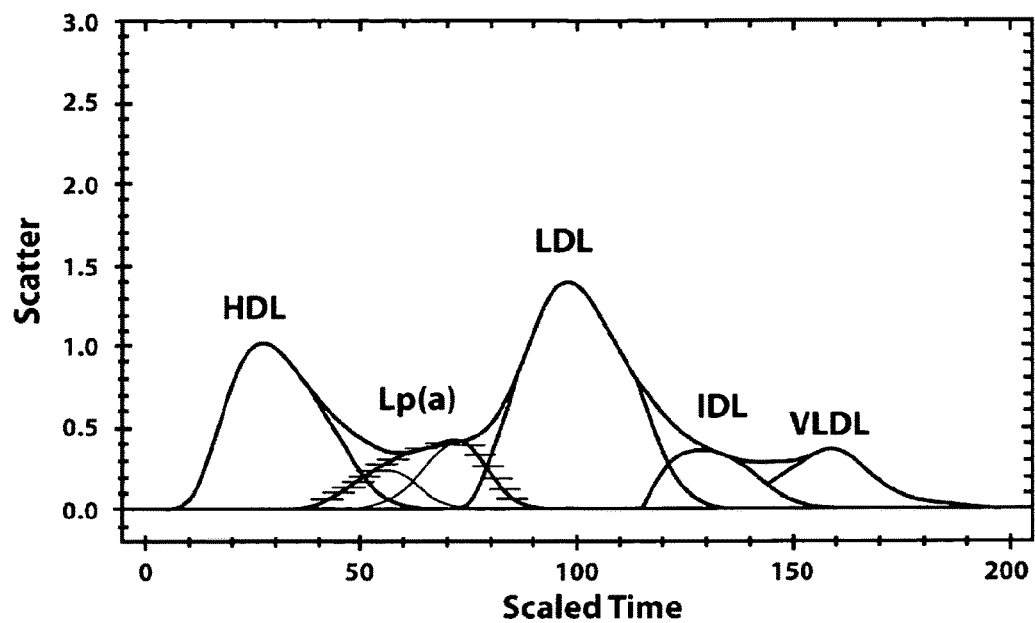
FIG. 17 shows the deconvoluted profile corresponding to the particle concentration profile shown in FIG. 13.
Figure 18:
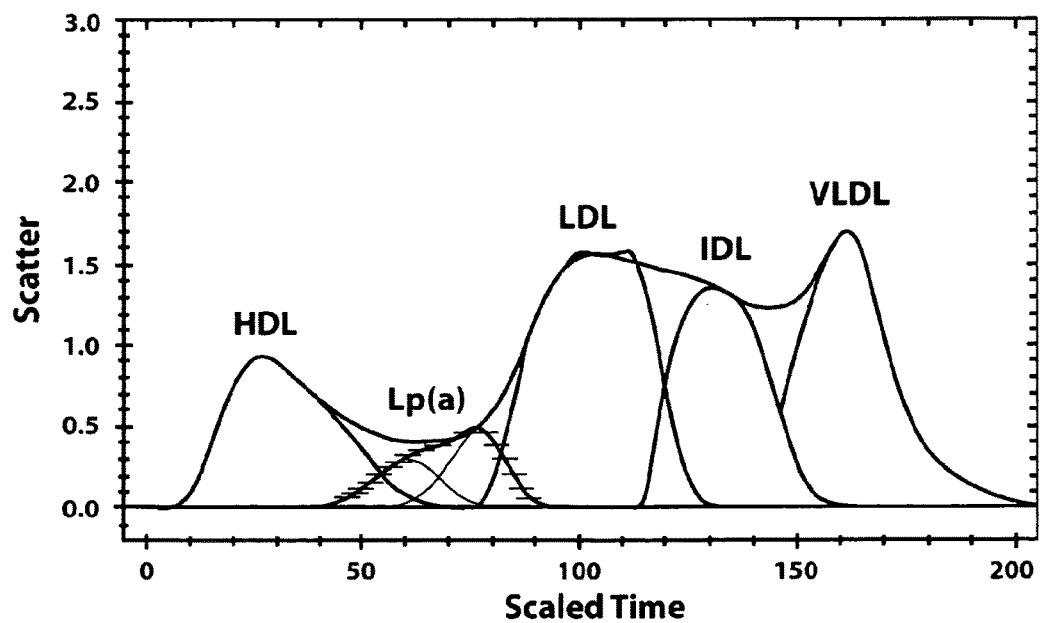
FIG. 18 shows the deconvoluted profile corresponding to the particle concentration profile shown in FIG. 14.
Figure 19:
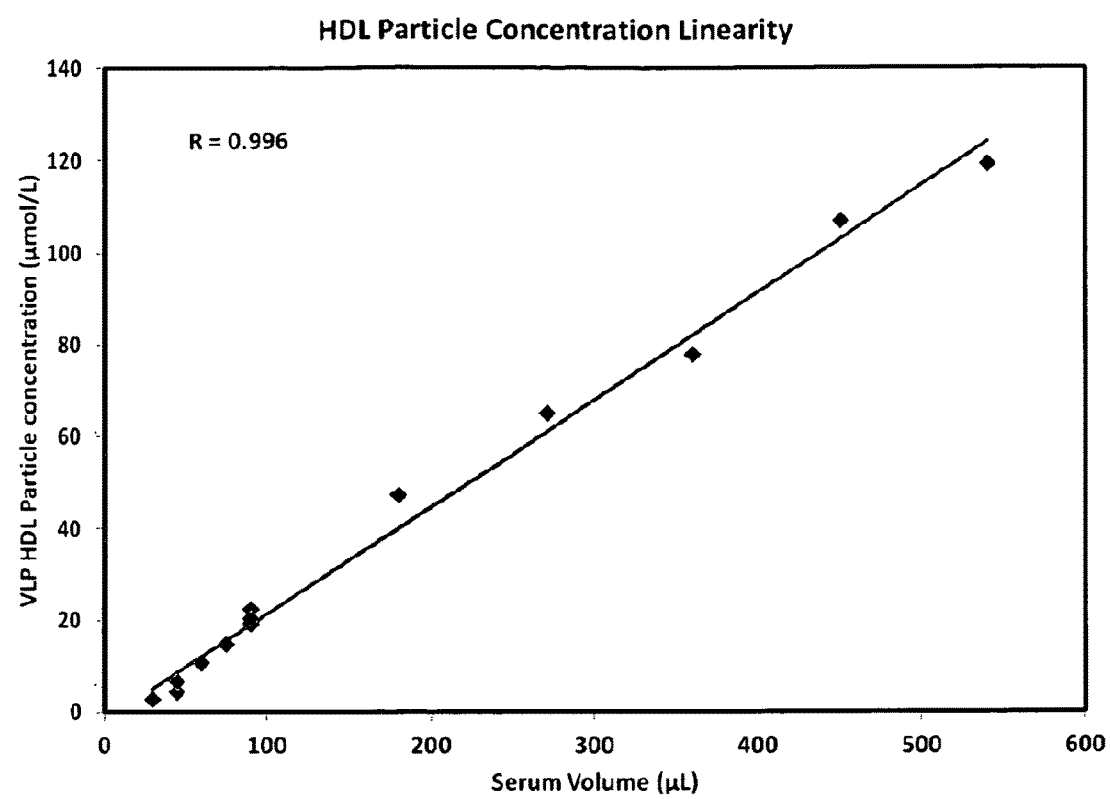
FIG. 19 shows a linearity graph for HDL.
Figure 20:
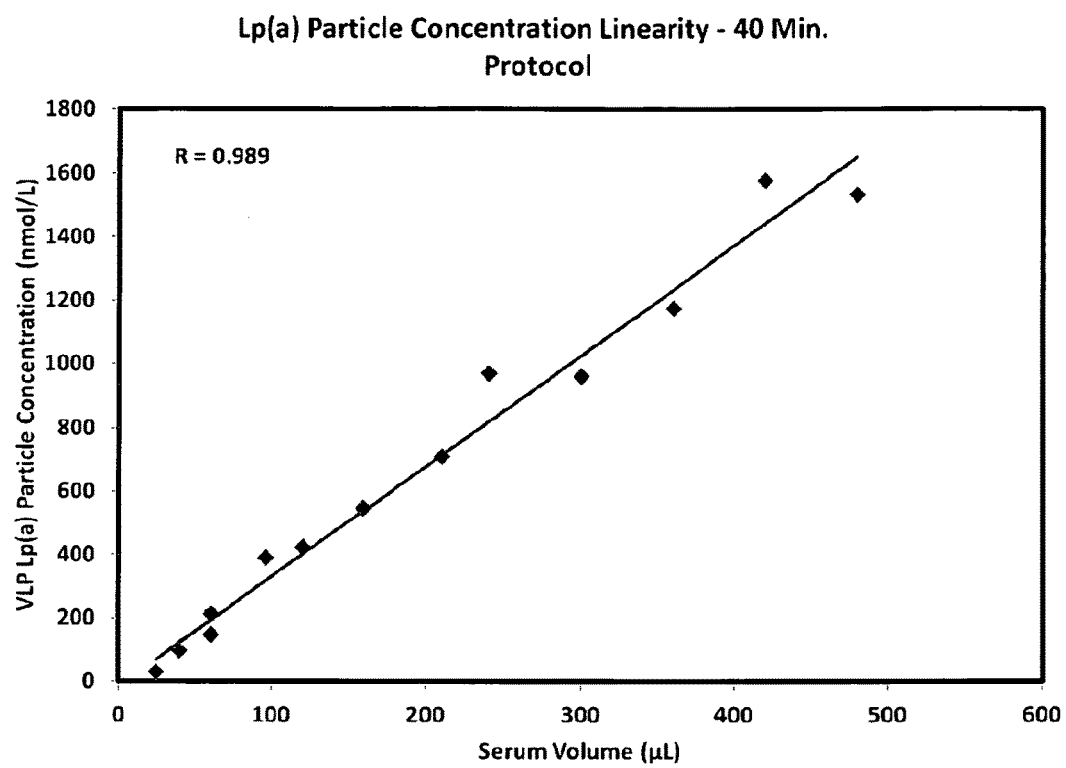
FIG. 20 shows a linearity graph for Lp(a).
Figure 21:
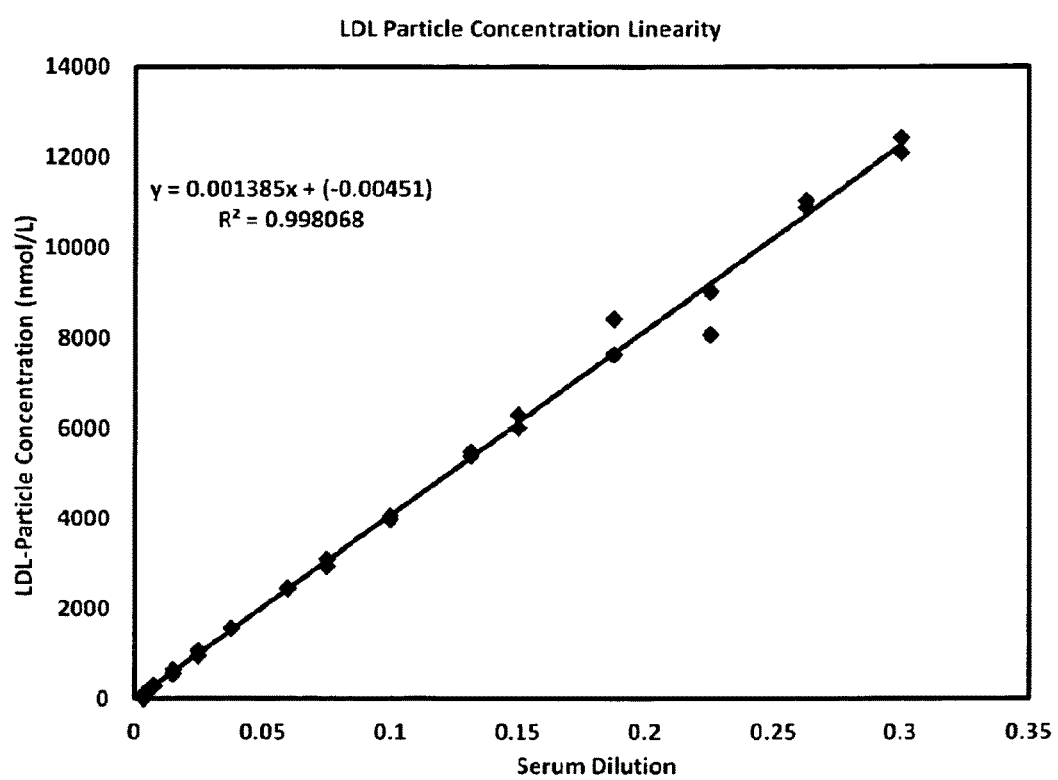
FIG. 21 shows a linearity graph for LDL.
Figure 22:
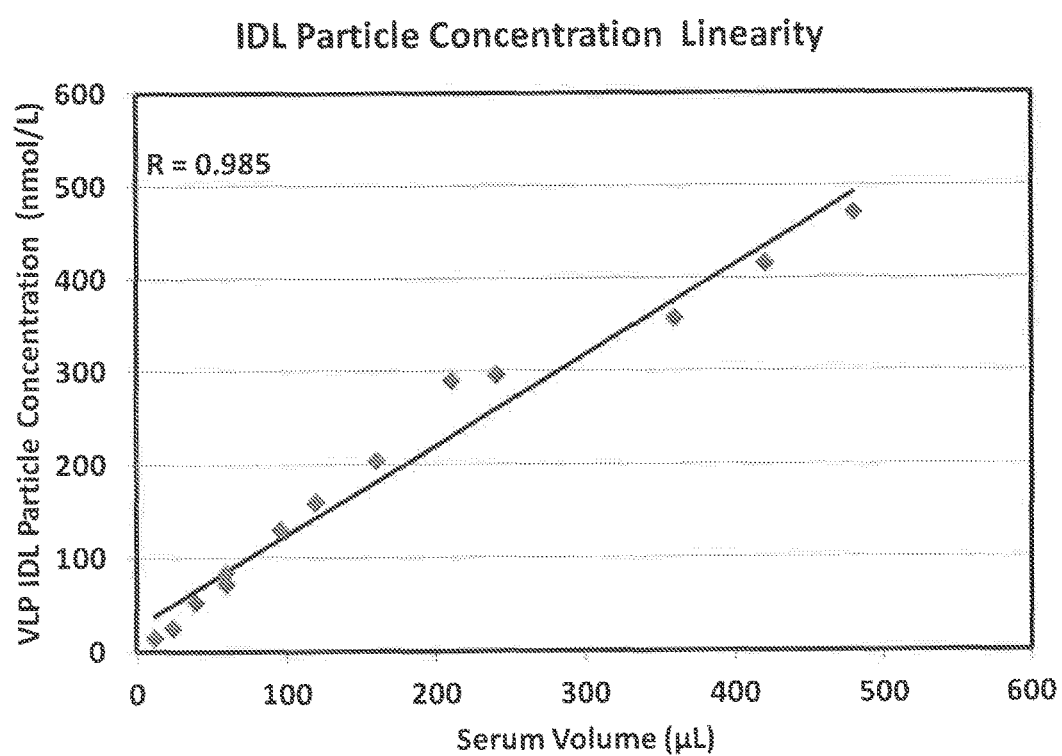
FIG. 22 shows a linearity graph for IDL.
Figure 23:
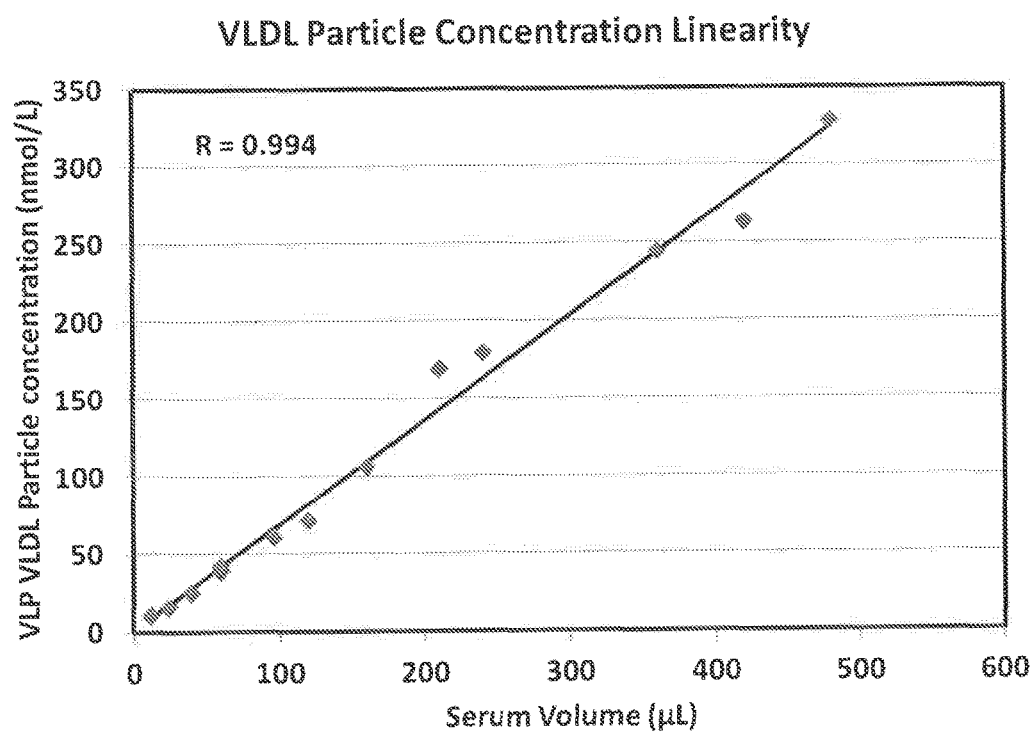
FIG. 23 shows a linearity graph for VLDL.

FIGS. 11-14 show the results of sample analysis using embodiments of the method and apparatus. FIG. 11 shows a normal lipid profile, showing three well-resolved peaks for the HDL, LDL, and VLDL fractions. FIG. 12 shows a high-LDL lipid profile, also showing three well-resolved peaks. FIG. 13 shows a high-Lp(a) lipid profile, in which the Lp(a) peak falls between the HDL peak and LDL peak; as can be seen the Lp(a) peak is quite visible. FIG. 14 shows a high-IDL lipid profile, in which a pronounced IDL peak falls between the LDL peak and VLDL peak. The deconvoluted profiles corresponding to FIGS. 11-14 are shown in FIGS. 15-18, respectively. The resulting deconvoluted profiles have three major peaks for fractions of decreasing density going from left to right (as the time variable increases) corresponding to the HDL, LDL, and VLDL; and two minor peaks corresponding to Lp(a) and IDL as described above.

Blank Spin

In order to assess interference due to solvents (KBr, saline, water, Cleanz™) and undissolved particles, a "blank" containing no serum (serum substituted with saline solution) was centrifuged and subjected to the lipoprotein counting protocol as described above. The blank profiles suggested a small drop in signal by KBr used for gradient preparation which was proportional to KBr concentration. Thus measurements from a blank run from the test sample were subtracted from the light scattering measurements for the lipoprotein fractions to correct. This process is embedded in the deconvolution algorithm.

Controls

To monitor the stability of the signal from day to day three pooled serum samples with increasing LDL-R particle counts (obtained from Solomon Park Research Laboratories, Seattle, Wash.) were run daily.

Precision

The precision and reproducibility of the lipoprotein particle count methods disclosed was also examined for each lipoprotein class.

For LDL, IDL and VLDL precision/reproducibility studies, 4 pools of samples were prepared. Pool 1 had a triglyceride concentration of 70 mg/dL and an LDL particle count of <1000 nmol/L. Pool 2 had a triglyceride concentration of 70 mg/dL and an LDL particle count of >1000 nmol/L. Pool 3 had a triglyceride concentration of 218 mg/dL and an LDL particle count of >1900 nmol/L. Pool4 had a triglyceride concentration of 320 mg/dL and an LDL particle count of >2100 nmol/L. For pools 1 and 2, 4 runs were made each day for 5 days, with each run containing 8 samples from each of pool 1 and 2 for a total of 160 samples. For pools 3 and 4, 3 runs were made each day for 5 days, with each run containing 8 samples from each of pool 3 and 4 for a total of 120 samples. For these studies samples were prepared and analyzed by the methods and apparatus described herein using the separation condition referenced as Condition 2 herein. Average LDL particle concentrations for pool 1 were 886 nmol/L, for pool 2 were 1386 nmol/L, for pool 3 were 1683 nmol/L and for pool 4 were 2125 nmol/L. Average IDL particle concentrations for pool 1 were 43 nmol/l, for pool 2 were 66 nmol/L, for pool 3 were 149 nmol/L and for pool 4 were 210 nmol/l. Average VLDL particle concentrations for pool 1 were 20 nmol/L, for pool 2 were 18 nmol/L, for pool 3 were 115 nmol/L and for pool 4 were 252 nmol/L. The results are expressed in coefficient of variation (% CV) within each day and between all days. The results for LDL, IDL and VLDL are shown below and show good reproducibility.

LDL-Particle Reproducibility (% CV)

| DAY | Pool 1 (% CV) | Pool 2 (% CV) | Pool 3 (% CV) | Pool 4 (% CV) |
|---|---|---|---|---|
| Day 1 | 2.4 | 2.8 | 5.1 | 7.4 |
| Day 2 | 3.6 | 2.8 | 5.9 | 6.3 |
| Day 3 | 2.1 | 3.1 | 5.5 | 5.7 |
| Day 4 | 2.4 | 2.9 | 6.7 | 6.6 |
| Day 5 | 2.8 | 2.8 | 5.9 | 6.7 |
| Between Days (i.e All Results) | 3.1 | 3.3 | 6.3 | 6.6 |

IDL-Particle Reproducibility (% CV)

| DAY | Pool 1 (% CV) | Pool 2 (% CV) | Pool 3 (% CV) | Pool 4 (% CV) |
|---|---|---|---|---|
| Day 1 | 5.0 | 3.6 | 11.3 | 5.4 |
| Day 2 | 7.2 | 6.0 | 16.3 | 8.2 |
| Day 3 | 4.2 | 4.3 | 9.4 | 8.1 |
| Day 4 | 8.6 | 5.4 | 13.0 | 7.8 |
| Day 5 | 5.1 | 4.8 | 11.4 | 7.4 |
| Between Days (i.e All Results) | 7.8 | 5.8 | 13.0 | 7.9 |

VLDL-Particle Reproducibility (% CV)

| DAY | Pool 1 (% CV) | Pool 2 (% CV) | Pool 3 (% CV) | Pool 4 (% CV) |
|---|---|---|---|---|
| Day 1 | 4.4 | 2.9 | 5.3 | 3.2 |
| Day 2 | 4.5 | 2.9 | 6.9 | 4.2 |
| Day 3 | 6.1 | 2.7 | 6.9 | 3.6 |
| Day 4 | 4.0 | 2.5 | 7.1 | 3.6 |
| Day 5 | 3.8 | 2.9 | 6.3 | 4.6 |
| Between Days (i.e All Results) | 4.7 | 2.9 | 6.7 | 4.2 |

For HDL precision/reproducibility studies, 2 pools of samples were prepared. Pool 1 had an apo AI concentration of 115 mg/dL (as measured by the Architect/Abbot immunoassay system). Pool 2 had an apo AI concentration of 255 mg/dL (as measured by the Architect/Abbot immunoassay system). For pools 1 and 2, 3 runs were made each day for 6 days, with each run containing 5 samples from each of pool 1 and 2 for a total of 90 samples. For these studies samples were prepared and analyzed by the methods and apparatus described herein using the separation condition referenced as Condition 3 herein. The results are expressed in coefficient of variation (% CV) within each day and between all days. The results for HDL are shown below and show good reproducibility.

HDL-Particle Reproducibility (% CV)

| DAY | Pool 1 (% CV) | Pool 2 (% CV) |
|---|---|---|
| Day 1 | 20.0 | 7.0 |
| Day 2 | 21.9 | 9.4 |
| Day 3 | 29.7 | 14.1 |
| Day 4 | 21.6 | 12.7 |
| Day 5 | 18.5 | 8.4 |
| Day 6 | 16.5 | 11.0 |
| Between Days (i.e All Results) | 24.0 | 11.9 |

For Lp(a) precision/reproducibility studies, 3 pools of samples were prepared. Pool 1 had an Lp(a) concentration of 27 nmol/L. Pool 2 had an Lp(a) concentration of 188 nmol/L. Pool 3 had an Lp(a) concentration of 300 nmol/L. For pools 1 to 3, 3 runs were made each day for 6 days, with each run containing 5 samples from each of pool 1 to 3 for a total of 90 samples. For these studies samples were prepare and analyzed by the methods and apparatus described herein using the separation condition referenced as Condition 4 herein. The results are expressed in coefficient of variation (% CV) within each day and between all days. The results for Lp(a) are shown below and show good reproducibility.

Lp(a)-Particle Reproducibility (% CV)

| DAY | Pool 1 (% CV) | Pool 2 (% CV) | Pool 3 (% CV) |
|---|---|---|---|
| Day 1 | 16.3 | 8.4 | 5.1 |
| Day 2 | 20.2 | 13.4 | 7.1 |
| Day 3 | 23.1 | 14.1 | 5.8 |
| Day 4 | 22.0 | 11.9 | 5.4 |
| Day 5 | 21.6 | 14.5 | 6.3 |
| Day 6 | 16.9 | 12.0 | 9.9 |

-continued

| DAY | Pool 1 (% CV) | Pool 2 (% CV) | Pool 3 (% CV) |
|---|---|---|---|
| Between Days (i.e All Results) | 25.4 | 14.2 | 7.7 |

Linearity

Linearity of lipoprotein particle measurements were determined for each of HDL, Lp(a), LDL, IDL and VLDL. For LDL, IDL and VLDL, the centrifugation condition used was Condition 2. For HDL, the centrifugation condition used was Condition 3. For Lp(a), the centrifugation condition used was Condition 4. The method was carried out as described herein using the apparatus described herein.

Generally, serial dilutions of a samples were made in the bottom layer of the density gradient solution (for LDL, IDL and VLDL, the bottom layer was a 1.21. g/ml KBr solution). Multiple dilutions were made ranging from 0.4% to 30%. Lipoprotein particle concentration measurements were performed in duplicate using the separation conditions for best resolution of each lipoprotein species and with the methods and apparatus disclosed herein. The resulting particle count for each lipoprotein was plotted with its corresponding serum dilution using a linear regression analysis method. Plots for HDL, Lp(a), LDL, IDL and VLDL are shown in FIGS. 19-23, respectively. The $R^2$ value for the plots were 0.996, 0.9890.998, 0.985 and 0.994, respectively for HDL, Lp(a), LDL, IDL and VLDL. This shows that lipoprotein particle measurement is linear up to the tested ranges.

Accuracy

The accuracy of the methods for determining lipoprotein particle concentration (number) was also evaluated. For LDL, two comparisons were made. First, comparison of average LDL particle concentration (number) was compared to serum apo B concentration. Second, comparison of average LDL particle concentration (number) was compared to LDL particle concentration (number) as measured by NMR.

Figure 24:
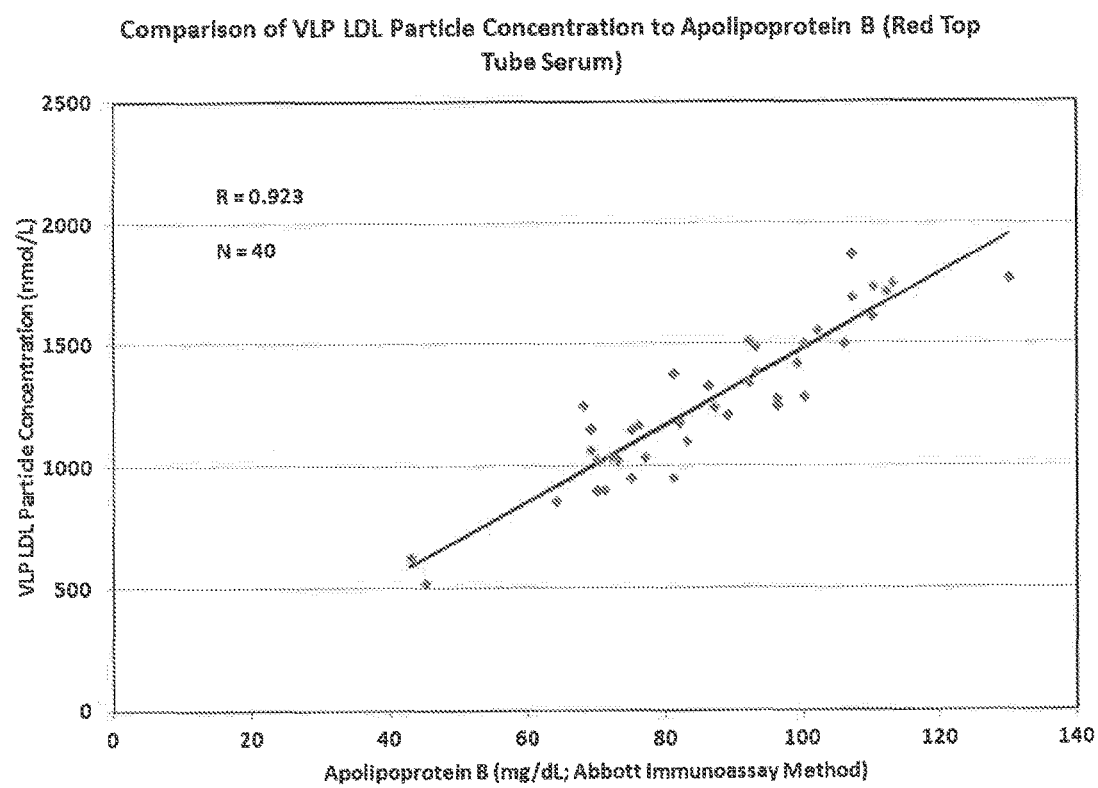
FIG. 24 shows a comparison of LDL particle number as determined by the methods described herein (using Condition 2 as the centrifugation condition) to apo B concentration as determined by the Abbott/Architect C8000 immunoassay.

It is known that each atherogenic lipid particle, including LDL, contains one apo B molecule and therefore one can visualize direct comparison of LDL particle number to apo B concentration in an LDL fraction. A good correlation can be anticipated between LDL particle number and whole serum apo B, at least in normotriglyceridemic subjects (triglyceride<150 mg/dL), since >90% of apo B is known to be present in LDL particles. This correlation may be reduced as triglycerides concentration increases since each triglyceride-rich lipoprotein (IDL and VLDL) also contain one molecule of apo B. Therefore, LDL particle number as determined by the methods described herein (using Condition 2 as the centrifugation condition) was compared with serum apo B concentration in serum samples (SST) collected from 40 apparently healthy individuals (similar results were obtained when Condition 1 was used; data not shown). The turbidimetry immunoassay by Abbott/Architect C8000 was used for serum apo B measurement. FIG. 24 shows a plot of the comparison of average LDL particle number obtained and apo B obtained from Abbott/Architect C8000. The above results show a good correlation between LDL average particle number and serum apo B concentration.

Figure 25:
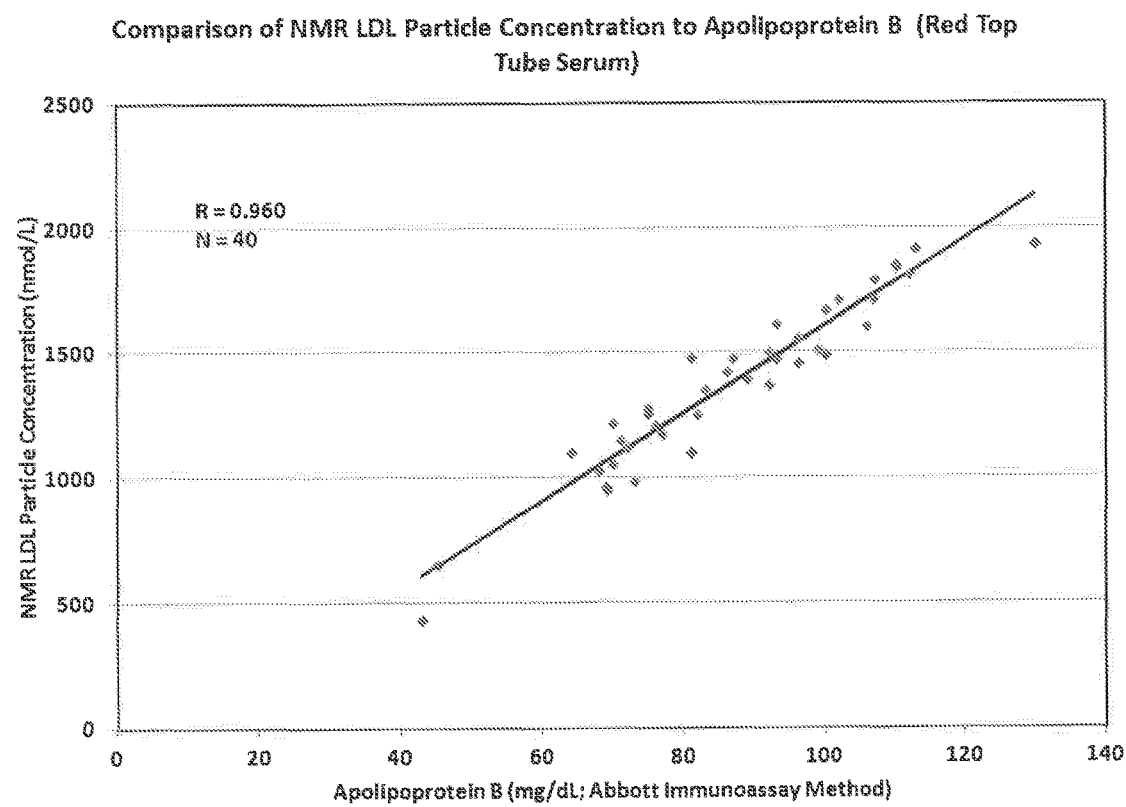
FIG. 25 shows a comparison of LDL particle number as determined by the methods described herein (using Condition 2 as the centrifugation condition) to LDL particle number as determined by an NMR assay (LipoScience).

In addition, average LDL particle number was compared to an NMR technique. The comparison was made with the same 239 samples described above. The results of this comparison (average LDL number obtained from 3 separate instruments and NMR results) are shown in FIG. 25. The above results show a reasonable agreement between the two methods. It should be noted that LDL particle count measured by the methods described herein does not include Lp(a) and IDL, which are generally considered components of LDL. It is not clear whether LDL particle numbers from NMR method includes Lp(a) and or IDL. Thus, a high correlation and agreement between the two methods may not be expected. Moreover, the two methods are based on entirely two different principles.

For IDL and VLDL fractions, comparison between the average lipoprotein particle counts was made using the concentration of cholesterol measure in the IDL and VLDL fractions as determined by the VAP Assay (Atherotech, Inc., Birmingham, Ala.; methods described in U.S. Pat. Nos. 5,284,773 and 5,633,168, which are hereby incorporated by reference for such teaching). IDL and VLDL particle number as determined by the methods described herein (using Condition 2 as the centrifugation condition) was compared with cholesterol content as determined by the VAP assay.

Figure 26:
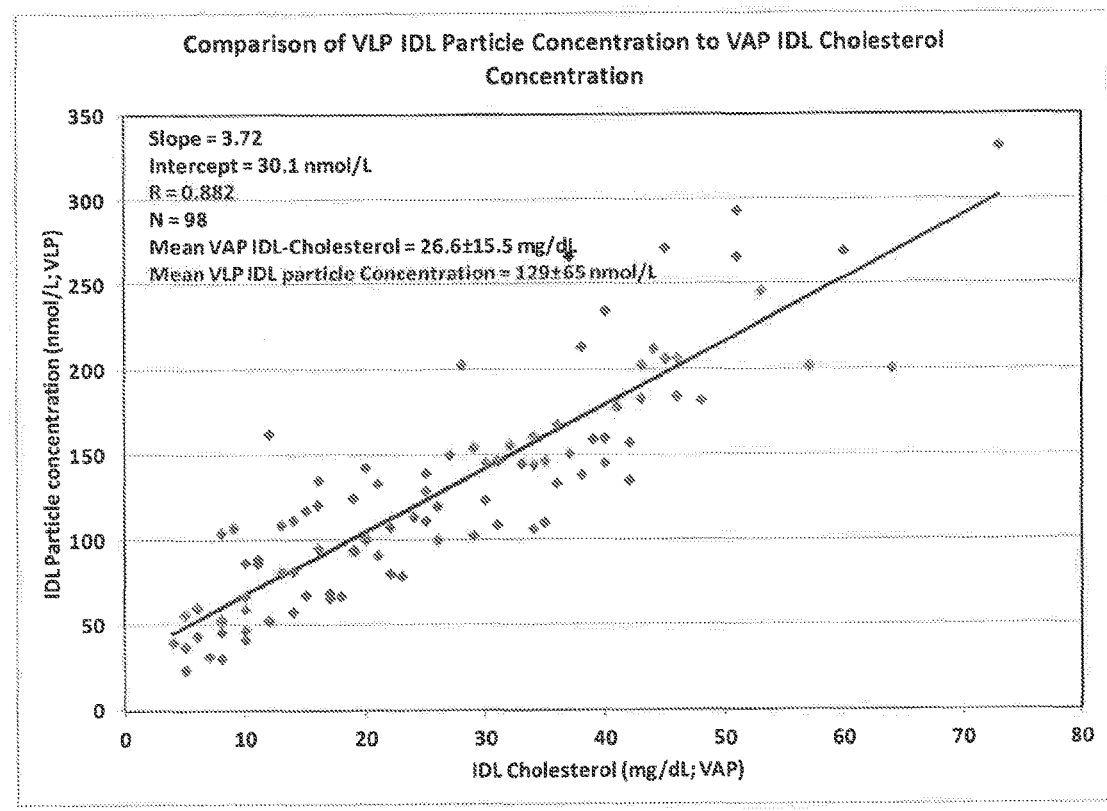
FIG. 26 shows a comparison of IDL particle number as determined by the methods described herein (using Condition 2 as the centrifugation condition) as compared to cholesterol concentration in the IDL peak as determined by the VAP assay (Atherotech, Inc.).
Figure 27:
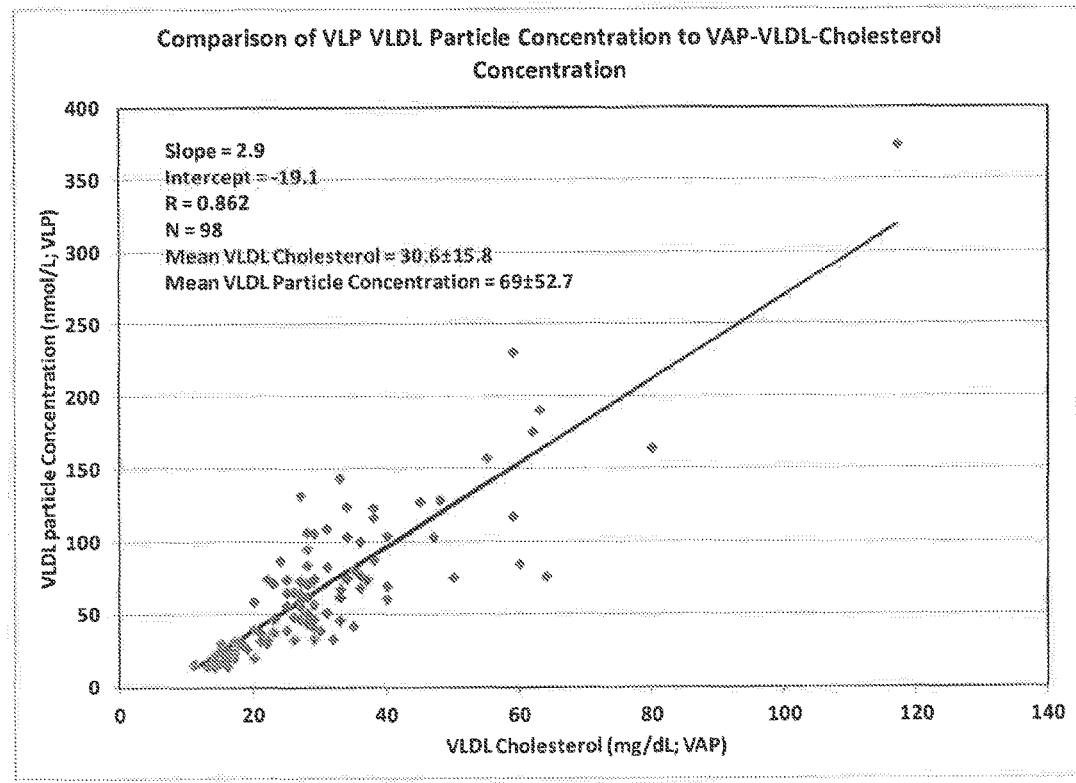
FIG. 27 shows a comparison of VLDL particle number as determined by the methods described herein (using Condition 2 as the centrifugation condition) as compared to cholesterol concentration in the VLDL peak as determined by the VAP assay (Atherotech, Inc.).

The results are shown in FIGS. 26 and 27 for IDL and VLDL, respectively. As can be seen in FIG. 26, the comparison of IDL particle concentration (number) versus IDL cholesterol produced a linear plot with a slope of 3.72 and an R of 0.882. As can be seen in FIG. 27, the comparison of VLDL particle concentration (number) versus VLDL cholesterol produced a linear plot with a slope of 2.9 and an R of 0.862. Both results show a good correlation between IDL/VLDL particle number and cholesterol.

Figure 28:
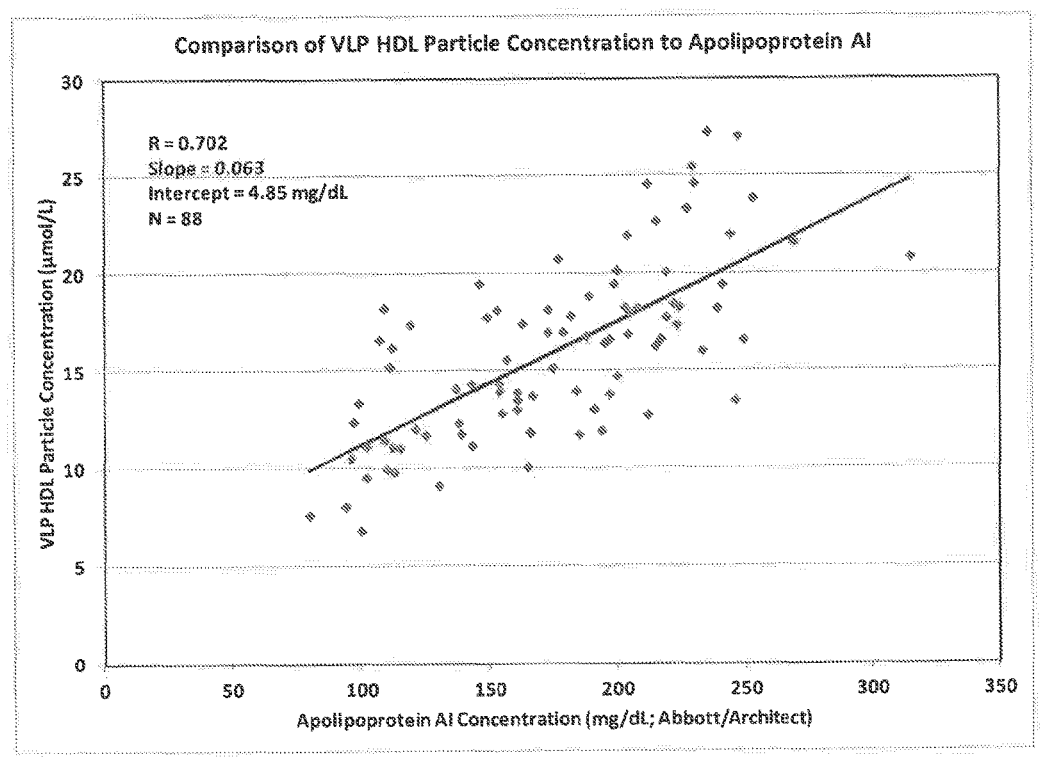
FIG. 28 shows a comparison of HDL particle number as determined by the methods described herein (using Condition 3 as the centrifugation condition) to Apo AI concentration as determined by the Abbott/Architect C8000 immunoassay.

For HDL, HDL particle number as determined by the methods described herein (using Condition 3 as the centrifugation condition) was compared with serum apo AI concentration in serum samples (SST) collected from 88 individuals. The turbidimetry immunoassay by Abbott/Architect C8000 was used for serum apo AI measurement. FIG. 28 shows a plot of the comparison of average HDL particle number and apo AI obtained from Abbott/Architect C8000. The above results show a good correlation between HDL average particle number and serum apo AI concentration. While the R value reported for HDL (0.63) was not as high as that reported for LDL, the lower correlation observed is likely a function of the heterogeneous nature of apo AI distribution on HDL particles as compared to the homogenous distribution of apo B on LDL particles.

Figure 29:
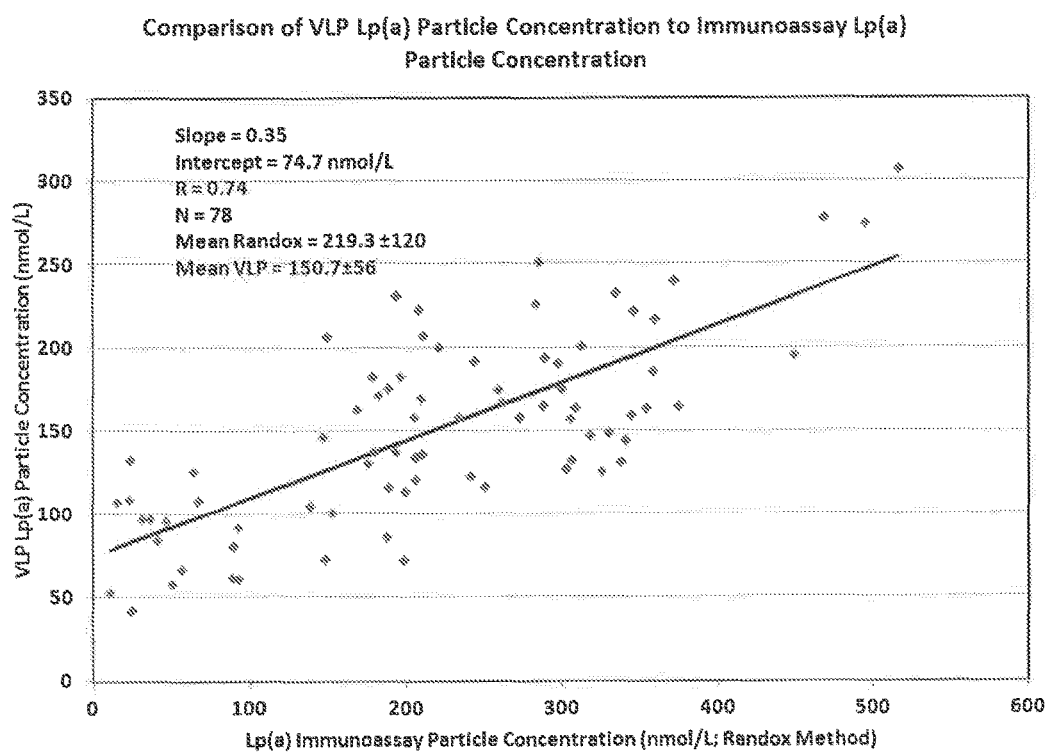
FIG. 29 shows a comparison of Lp(a) particle number as determined by the methods described herein (using Condition 4 as the centrifugation condition) as compared with Lp(a) concentration as determined by the Randox Laboratories Lp(a) immunoassay.

For Lp(a), Lp(a) particle number as determined by the methods described herein (using Condition 4 as the centrifugation condition) was compared with Lp(a) concentration in serum samples (SST) collected from 78 individuals. The Lp(a) immunoassay by Randox Laboratories was used to measure Lp(a). FIG. 29 shows a plot of the comparison of average Lp(a) particle number as determined by the methods described herein and Lp(a) results obtained from the Randox immunoassay. The above results show a good correlation between Lp(a) average particle number and serum Lp(a) concentration.

Deconvolution

In one embodiment, the deconvolution algorithm used herein is based on plurality of basis of curves that can be manipulated to provide a best fit to any given lipoprotein profile. In one embodiment, there are multiply basis curves for a given lipoprotein class. In an alternate embodiment, there is a single curve for a given lipoprotein class. The number and location of the subcurves is based, in one embodiment, on empirical observation and testing with lipoprotein samples to determine a baseline for the analysis. In a particular embodiment, 14 basis curves are used. In a particular embodiment, 14 basis curves are used, with 5 curves used for the HDL class, 1 curve for the Lp(a) class, 3 curves for the LDL class, 2 curves for the IDL class and 3 curves for the VLDL class.

The fit is based on non-linear equations and involves one or more iterations to converge to a solution. The curves are based on a four parameter Weibull curve that has been used to describe particle size distribution. The Weibull equation is a well known equation commonly used in statistical and reliability calculations. The use of the Weibull equation has the following advantages. First, it requires only four parameters. Second, the equation assumes a wide continuum of curve shapes and sizes. Third, the area under any unit amplitude curve is always =1.00. Fourth, the equation is analytically differentiable on all four parameters (i.e., the curves are smooth)

Using the Weibull equation, the curves are all defined at any point X by a single equation (Equation 4), where: α controls the curve width; β control the curve $$\frac{\beta}{\alpha^\beta} \cdot (X - \mu)^{\beta-1} \cdot e^{-\left(\frac{X-\mu}{\alpha}\right)^\beta}$$

shape; and μ controls the curve location.

Figure 30:
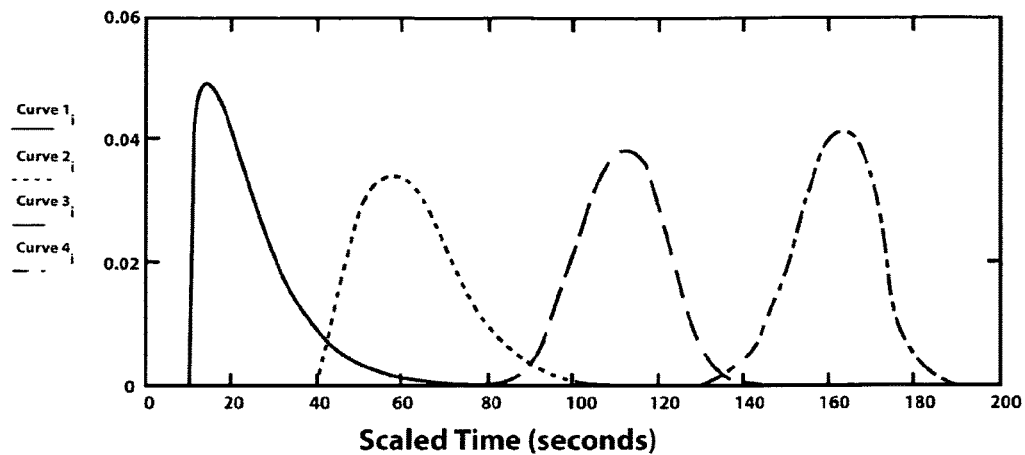
FIG. 30 shows an exemplary set of curves generated by varying the parameters of the Weibull equation.

By simply varying the parameter values, a wide variety of curve shapes and sizes is possible. Four example curves generated using the variables below are shown in FIG. 30

1 A:=1.0 α:=15 β:=1.25 μ:=10 Curve1$_i$:=Weibull (A, α, β, μX$_i$)

2 A:=1.0 α:=25 β:=2 μ:=40 Curve2$_i$:=Weibull (A, α, β, μX$_i$)

3 A:=1.0 α:=35 β:=3.5 μ:=80 Curve3$_i$:=Weibull (A, α, β, μX$_i$)

4 A:=1.0 α:=45 β:=5 μ:=120 Curve4$_i$:=Weibull (A, α, β, μX$_i$)

To account for minor process changes and variation in pump speeds, viscosity, and temperature and other factors, the time scale of the profiles is normalized to a common scale. In one embodiment, the scale is arbitrarily set to 0-200. Each profile is segmented based on signals from the data set that uses the expected timing from separation procedure (such as ultracentrifugation) and morphological features found in the profile shapes.

Because the curves are non-linear, a simple linear regression is not sufficient to deconvolute the curves. In one embodiment, the Levenberg Marquadt is used to deconvolute the curves. This algorithm uses a search and step method to find a good fit for each curve. In one embodiment, all four parameters can be constrained to fit within a specified range. In particular, the range of motion along the X-Axis for each curve is constrained so that the curves occupy a defined position based on the class of lipoprotein represented by the curve. In addition, the amplitude parameters are required to be positive.

Figure 31:
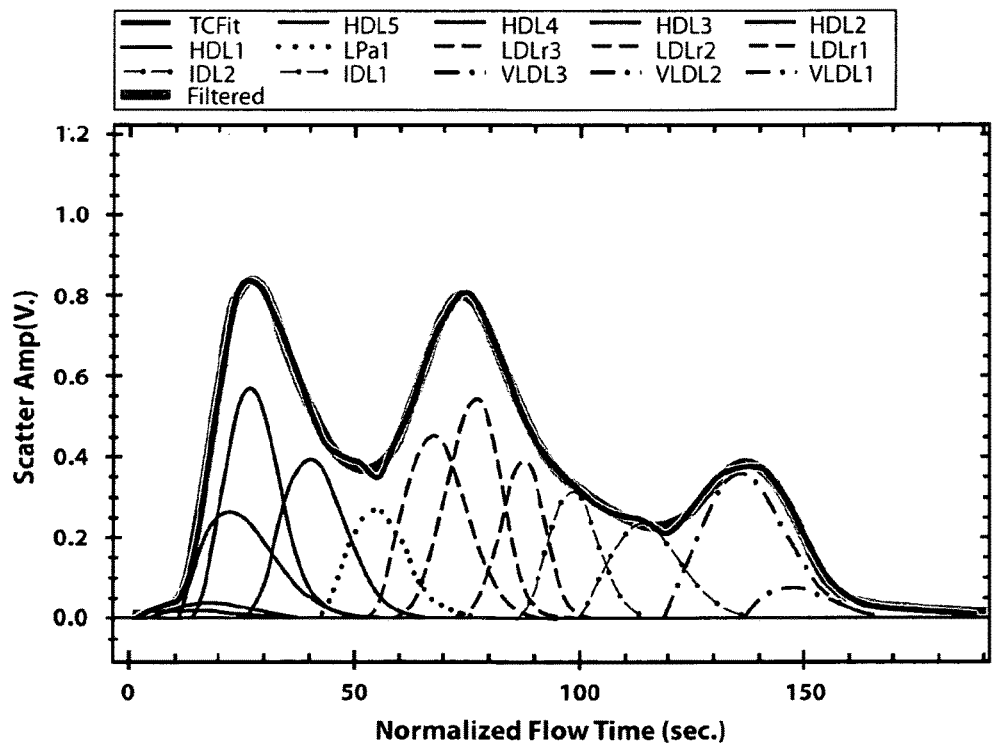
FIG. 31 shows an example of deconvolution of a particle concentration profile collected with a light scattering detector, with the continuous profile being deconvoluted into 14 subcurves.
Figure 32:
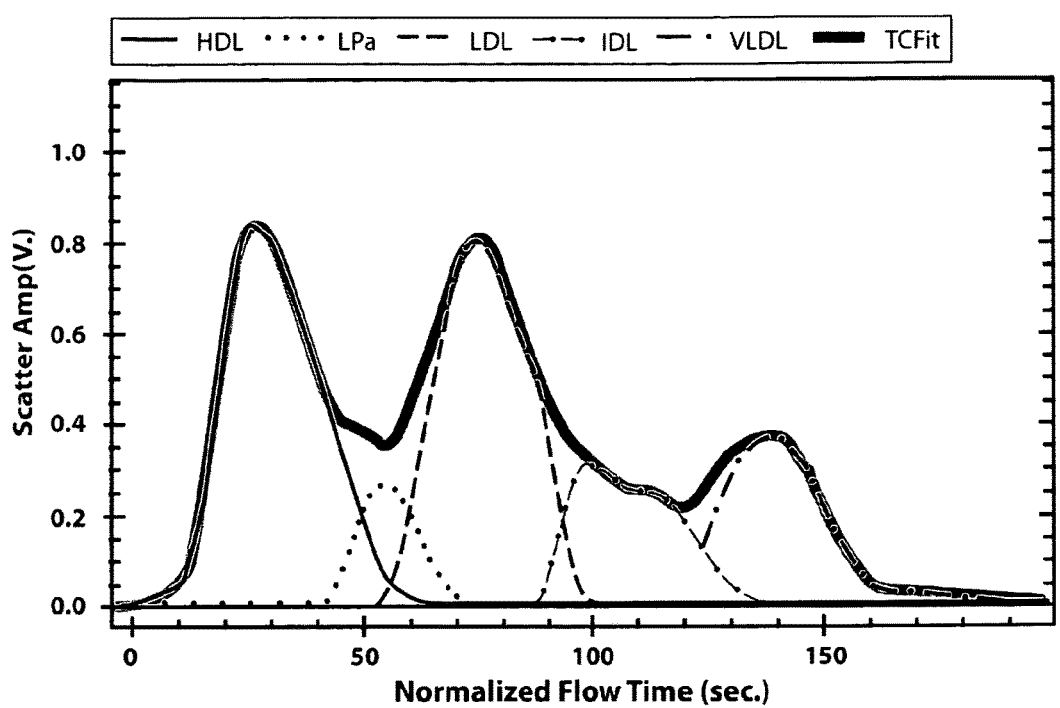
FIG. 32 shows an example of grouping and summing the subcurves shown in FIG. 31 into higher level curves representative of the lipoprotein classes.

An example fit is shown below. It shows all 14 of the minor subcurves. Note the varying shapes and amplitudes (FIG. 31). In FIG. 31 (as well as FIG. 32 below), the dark line is the particle concentration profile collected with a light scattering detector, which is deconvoluted into the various subcurves below. After the minor subcurves are generated, they are grouped and summed into higher level curves. In this case, curves for the HDL, LPa, LDL, IDL, and VLDL lipoprotein classes (FIG. 32). The area under each higher level curve is then determined as described herein.

L. Conclusions

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. It is to be understood that any given elements of the disclosed embodiments may be embodied in a single structure, a single step, a single substance, or the like. Similarly, a given element of the disclosed embodiment may be embodied in multiple structures, steps, substances, or the like. Any section headings herein are provided only for consistency with the suggestions of 37 C.F.R. §1.77 or otherwise to provide organizational queues. These headings shall not limit or characterize the disclosure set forth herein.

What is claimed:

1. A method of measuring lipoprotein particle number in a sample, the method comprising:
  a. separating a LDL fraction, an IDL fraction and a VLDL fraction in the sample by centrifugation;
  obtaining a photometric measurement in the LDL fraction;
  c. calculating a LDL particle count for the LDL fraction that is a function of the photometric measurement;
  d. obtaining a photometric measurement in the IDL fraction;
  e. calculating an IDL particle count for the IDL fraction that is a function of the photometric measurement in the IDL fraction;
  f. obtaining a photometric measurement in the VLDL fraction;
  g. calculating an VLDL particle count for the VLDL fraction that is a function of the photometric measurement in the VLDL fraction;
  h. separating at least one additional lipid fraction in the sample by centrifugation, the at least one additional lipid fraction selected from the group consisting of: a Lp(a) fraction and an HDL fraction;
  i. obtaining a photometric measurement in the at least one additional lipid fraction; and
  j. calculating a particle count for the at least one additional lipid fraction, wherein the particle count is a function of the photometric measurement in the at least one additional lipid fraction.

2. The method of claim 1, wherein the at least one additional lipid fraction is, an Lp(a) fraction.

3. The method of claim 1, wherein the at least one additional lipid fraction is a HDL fraction.

4. The method of claim 1, wherein the at least one additional lipid fraction is an Lp(a) fraction and an HDL fraction.

5. The method claim 1, wherein the function is an approximately linear function.

6. The method of claim 1, wherein separation is accomplished using density-gradient centrifugation.

7. The method of claim 1, wherein the sample is contained in a sample vessel, and further comprising sampling the sample vessel from the bottom so as to collect the fractions in descending order of density.

8. The method of claim 7, in which the LDL measurement is obtained before the IDL measurement is obtained, and in which the VLDL measurement is obtained after the LDL measurement is obtained.

9. The method of claim 1, wherein the sample is selected from the group consisting of: a blood sample and a blood serum sample.

10. A method of measuring lipoprotein particle number in a sample, the method comprising:
    a. separating an LDL fraction, an HDL fraction, an Lp(a), an IDP fraction and a VLDL fraction from the sample by centrifugation;
    b. obtaining a photometric measurement in the LDL fraction;
    c. calculating an LDL particle count for the LDL fraction that is a function of the photometric measurement in the LDL fraction;
    d. obtaining a photometric measurement in the HDL fraction;
    e. calculating an HDL particle count for the HDL fraction that is a function of the photometric measurement in the HDL fraction;
    f. obtaining a photometric measurement in the Lp(a) fraction;
    g. calculating an Lp(a) particle count for the Lp(a) fraction that is a function of the photometric measurement in the Lp(a) fraction;
    h. obtaining a photometric measurement in the IDL fraction;
    i. calculating an IDL particle count for the IDL fraction that is a function of the photometric measurement in the IDL fraction;
    k. obtaining a photometric measurement in the VLDL fraction; and
    l. calculating an VLDL particle count for the VLDL fraction that is a function of the photometric measurement in the VLDL fraction.

11. The method claim 10, wherein the function is an approximately linear function.

12. The method of claim 10, wherein separation is accomplished using density-gradient centrifugation.

13. The method of claim 10, wherein the sample is contained in a sample vessel, and comprising sampling the sample vessel from the bottom so as to collect the fractions in descending order of density.

14. The method of claim 13, in which the Lp(a) measurement is obtained after the HDL measurement is obtained, in which in which the LDL measurement is obtained after the Lp(a) measurement is obtained, in which the IDL measurement is obtained after the LDL measurement is obtained, and in which the VLDL measurement is obtained after the IDL measurement is obtained.

15. The method of claim 10, wherein the sample is selected from the group consisting of: a blood sample and a blood serum sample.

* * * * *